US012602798B2

(12) United States Patent
Xia et al.

(10) Patent No.: US 12,602,798 B2
(45) Date of Patent: Apr. 14, 2026

(54) METHOD AND APPARATUS FOR GENERATING SUBJECT-SPECIFIC MAGNETIC RESONANCE ANGIOGRAPHY IMAGES FROM OTHER MULTI-CONTRAST MAGNETIC RESONANCE IMAGES

(71) Applicant: University of Leeds, Leeds (GB)

(72) Inventors: Yan Xia, Leeds (GB); Nishant Ravikumar, Leeds (GB); Alejandro Federico Frangi, Leeds (GB)

(73) Assignee: University of Leeds (GB)

( * ) Notice: Subject to any disclaimer, the term of this patent is extended or adjusted under 35 U.S.C. 154(b) by 273 days.

(21) Appl. No.: 18/242,982

(22) Filed: Sep. 6, 2023

(65) Prior Publication Data

US 2025/0078290 A1 Mar. 6, 2025

(51) Int. Cl.
| | |
|---|---|
| *G06T 7/00* | (2017.01) |
| *G06T 3/40* | (2006.01) |
| *G06T 7/32* | (2017.01) |
| *G16H 30/40* | (2018.01) |

(52) U.S. Cl.
CPC ................. *G06T 7/32* (2017.01); *G06T 3/40* (2013.01); *G16H 30/40* (2018.01); *G06T 2207/10088* (2013.01); *G06T 2207/20081* (2013.01); *G06T 2207/20084* (2013.01); *G06T 2207/20212* (2013.01); *G06T 2207/30016* (2013.01); *G06T 2207/30101* (2013.01)

(58) Field of Classification Search
CPC ... G06T 7/32; G06T 3/40; G06T 2207/10088; G06T 2207/20081; G06T 2207/20084; G06T 2207/20212; G06T 2207/30016; G06T 2207/30101; G16H 30/40
See application file for complete search history.

(56) References Cited

U.S. PATENT DOCUMENTS

| | | | | |
|---|---|---|---|---|
| 2020/0022610 A1* | 1/2020 | Zenge | .................... | G16H 40/63 |
| 2022/0058798 A1* | 2/2022 | Rubin | .................... | G06T 7/174 |
| 2022/0373630 A1* | 11/2022 | Dou | .................... | G06T 7/262 |

(Continued)

OTHER PUBLICATIONS

Olut, S. et al. "Generative Adversarial Training for MRA Image Synthesis Using Multi-contrast MRI". In: Rekik, I., Unal, G., Adeli, E., Park, S. (eds) Predictive Intelligence in Medicine. Prime 2018. Lecture Notes in Computer Science(), vol. 11121. Springer, Cham. (Year: 2018).*

(Continued)

*Primary Examiner* — Van D Huynh

(74) *Attorney, Agent, or Firm* — Shackelford, McKinley & Norton, LLP

(57) ABSTRACT

There is provided a computer-implemented method for synthesising magnetic resonance angiography (MRA) images from other types of inputted magnetic resonance (MR) images, in a subject-specific manner, the method comprising providing a conditional generative adversarial network (cGAN) that learns a combined latent representation of the inputted magnetic resonance images for each subject and learns to transform this combined latent representation to a magnetic resonance angiography image corresponding to that subject, providing a plurality of magnetic resonance (MR) images as input into the cGAN, and outputting a plurality of MRA images from the cGAN based on the plurality of inputted MR images.

13 Claims, 8 Drawing Sheets

(56) References Cited

U.S. PATENT DOCUMENTS

2022/0409161 A1 * 12/2022 Crabb ................. A61B 6/5264
2023/0326011 A1 * 10/2023 Cutforth ................... G06T 7/10
382/128

OTHER PUBLICATIONS

Dar, Salman UH, et al. "Image synthesis in multi-contrast MRI with conditional generative adversarial networks." IEEE transactions on medical imaging 38.10 (2019): 2375-2388. (Year: 2019).*

Yan Xia et al., Virtual high-resolution MR angiography from non-angiographic multi-contrast MRIs: synthetic vascular model populations for in-silico trials, Medical Image Analysis, vol. 87, Published online on Apr. 20, 2023, 102814.

* cited by examiner

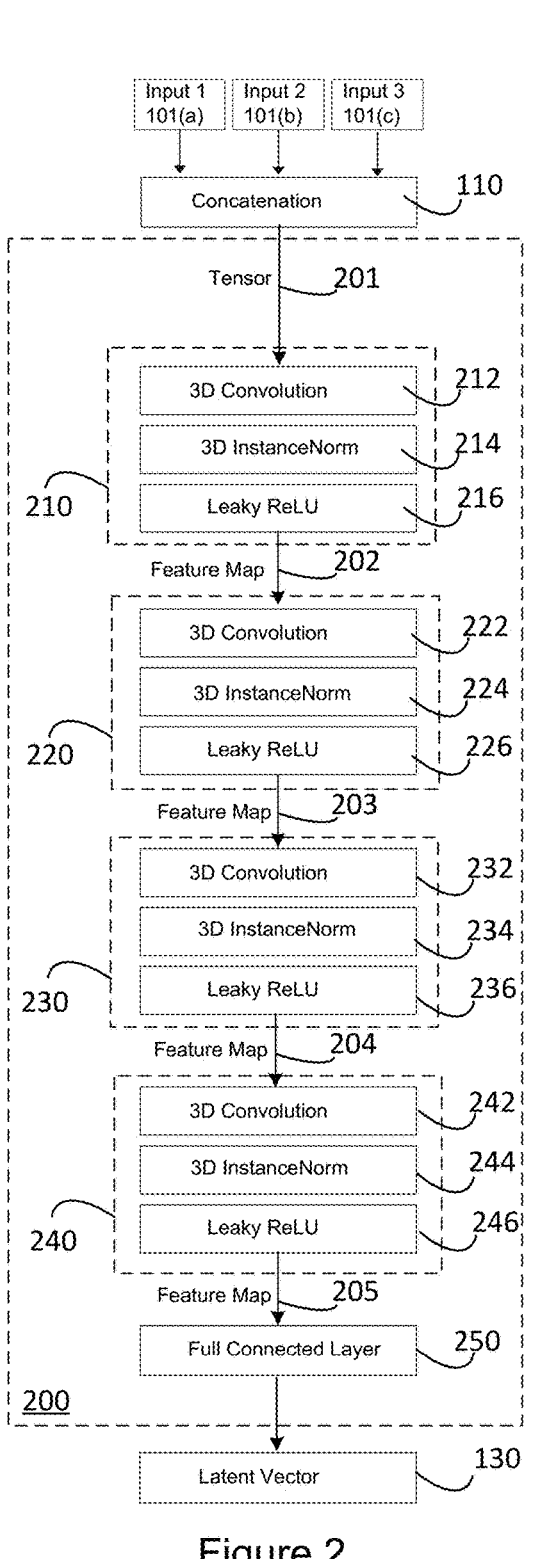

Input 1 101(a)    Input 2 101(b)    Input 3 101(c)

Concatenation — 110

Tensor — 201

3D Convolution — 212
3D InstanceNorm — 214
Leaky ReLU — 216
210

Feature Map — 202

3D Convolution — 222
3D InstanceNorm — 224
Leaky ReLU — 226
220

Feature Map — 203

3D Convolution — 232
3D InstanceNorm — 234
Leaky ReLU — 236
230

Feature Map — 204

3D Convolution — 242
3D InstanceNorm — 244
Leaky ReLU — 246
240

Feature Map — 205

Full Connected Layer — 250

200

Latent Vector — 130

Figure 2

Latent Vector — 130

Feature Map reshaping operation — 302

305

ResBlock — 400
310
Up-sampling — 311

304

ResBlock — 401
320
Up-sampling — 312

303

ResBlock — 402
330
Up-sampling — 313

302

ResBlock — 403
340
Up-sampling — 314

301

3D Convolution — 350

Tanh Activation Layer — 360

300

Final Output — 144

Figure 3

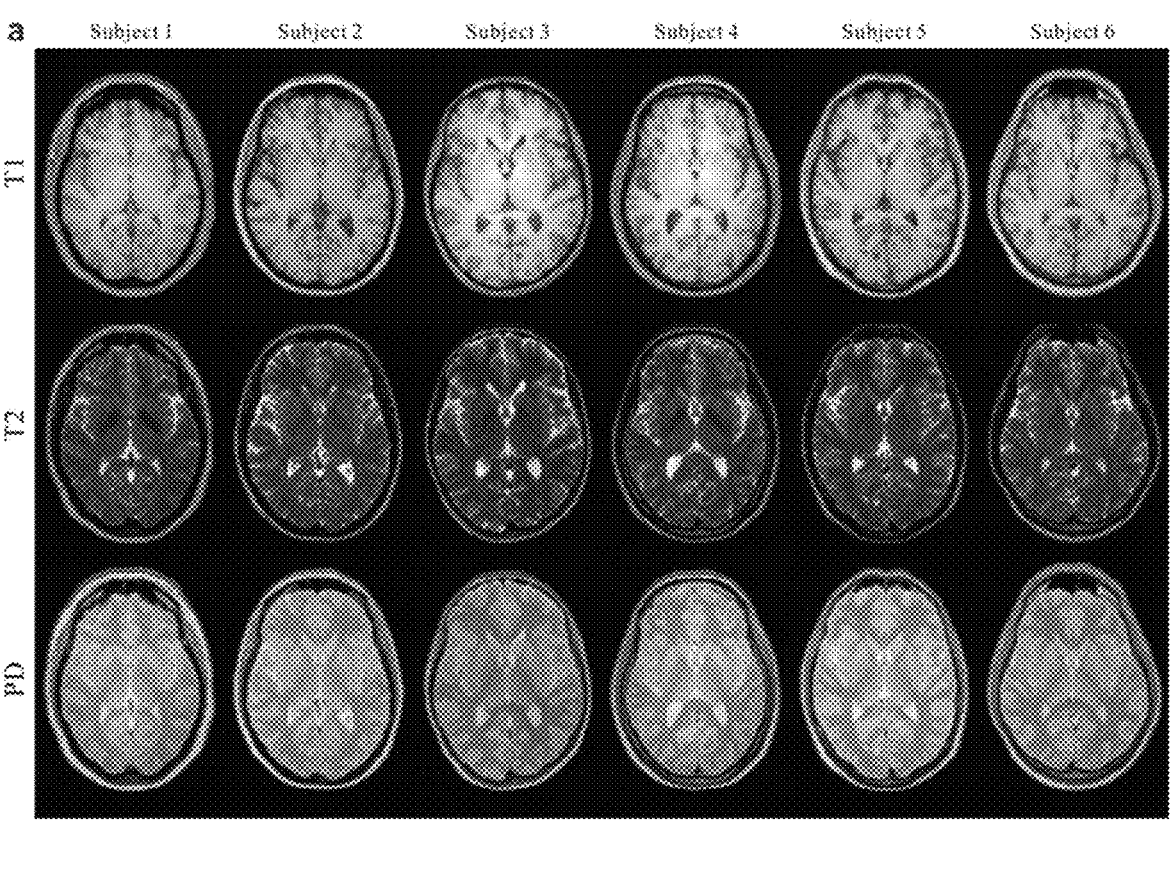
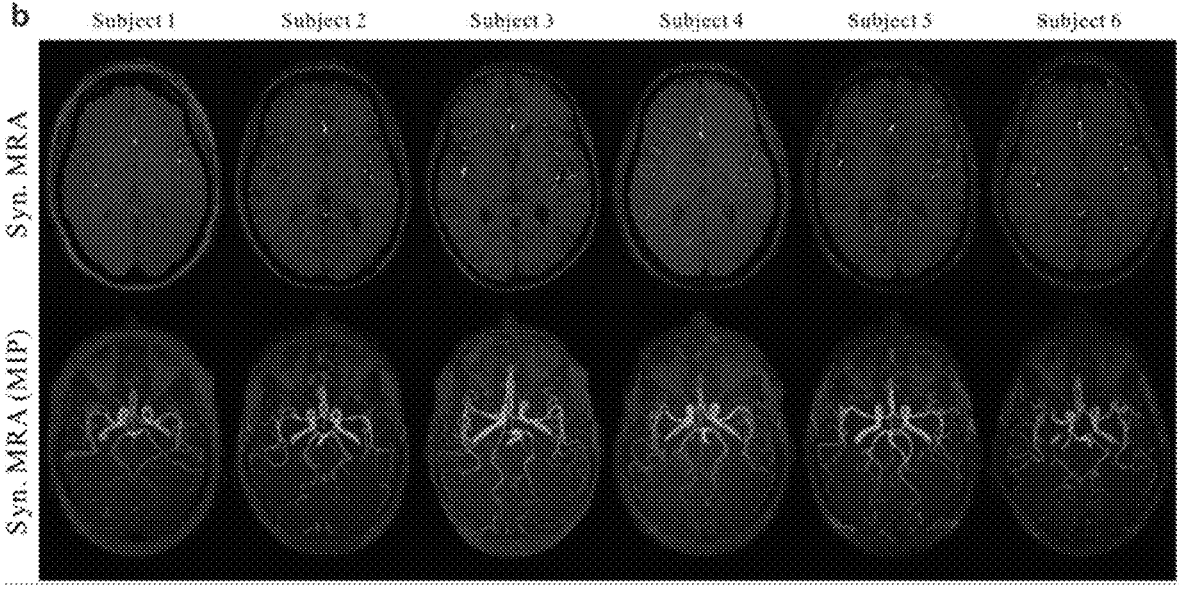
Figure 10

METHOD AND APPARATUS FOR GENERATING SUBJECT-SPECIFIC MAGNETIC RESONANCE ANGIOGRAPHY IMAGES FROM OTHER MULTI-CONTRAST MAGNETIC RESONANCE IMAGES

FIELD OF INVENTION

The present invention relates to a computer-implemented method, computer program and apparatus for generating subject-specific magnetic resonance angiography (MRA) images of the brain.

BACKGROUND OF THE INVENTION

Developing personalised diagnostic, prognostic, and therapeutic strategies is the central tenet of precision medicine, requiring characterisation and accommodation of inter-patient variability across the clinical decision-making pathway. This is crucial for improving patient safety and quality of care, maximising treatment efficacy, improving the efficiency of healthcare systems and ultimately, delivering the promised healthcare of the future. Three key enabling technologies for precision medicine have seen significant advances in recent years, namely: (i) scalable data sharing and computational infrastructure to collect, curate, distribute, and analyse multi-modal data of individual patients (as evidenced by large-scale population imaging initiatives, e.g. UK Biobank, German National Cohort, etc.); (ii) creation of digital twin or virtual patient cohorts, that are faithful representations of anatomy and physiology observed in real (target) patient populations; and (iii) generation of in-silico (through modelling and simulation) evidence, for assessing medical product safety and efficacy through so-called in-silico trials (ISTs).

ISTs simulate pathological biophysical phenomena and their corresponding therapies in either a cohort of digital twins or a cohort of virtual patients, to support the development and evaluation of medical devices, drugs and treatment strategies. While regulatory approval of novel devices and drugs have required in-vitro and in-vivo evidence of safety and efficacy in the past, regulatory agencies have begun accepting in-silico evidence to complement the former in-vivo. In-silico evidence is generated by conducting ISTs using digital twin and/or virtual patient cohorts and biophysical simulations of virtual interventions/treatments. These areas of research and innovation are thus inexorably intertwined, as generating sufficient evidence through ISTs requires: scalable computational infrastructure to execute complex modelling and simulation workflows; availability of virtual patient or digital twin cohorts that capture sufficient inter-patient variability in anatomy and physiology, in the target populations of interest; and correspondingly, generating representative digital twin or virtual patient cohorts requires access to high-quality, large-scale, multi-modal patient data, that is fit for purpose.

Recent studies have demonstrated that ISTs can replicate and expand findings of real clinical trials. Other related studies have shown that ISTs can also generate evidence of safety of new treatment strategies, and better inform patient selection for evaluation of treatment safety and efficacy in real clinical trials. Of specific relevance to the present disclosure are in-silico studies focused on assessing cerebrovascular haemodynamics (also referred to as understanding the physics of blood flow in the brain or computational fluid dynamics analysis of blood flow in the brain) in healthy and pathological/abnormal/diseased populations, and ISTs focused on assessing performance of devices and/or drugs used to treat cerebrovascular abnormalities/pathologies such as aneurysms or stenosed arteries. Previous in-silico studies that have simulated and assessed blood flow in cerebral vasculature have been limited in sample size due to not having access to sufficient amount of data of the correct form, for example, they have only been able to access small sample sets ranging from tens (typical) to a few hundred patients/subjects.

MRA images may be used for characterising (i.e. extracting the geometry of vessels and assessing the extracted vessels quantitatively) whole-brain vasculature (i.e. blood vessels throughout the brain) in 3D, but are typically not included in standard scanning protocols/routine clinical examinations because of the long acquisition times required. Whereas other multi-contrast MR images, such as longitudinal relaxation time (T1)-weighted MR images, or transverse relaxation time (T2)-weighted MR images, or proton density (PD)-weighted MR images are acquired more often as part of routine clinical examinations.

SUMMARY

Accordingly, a purpose of the present disclosure is to enable subject-specific synthesis of magnetic resonance angiography (MRA) images, given other multi-contrast MR images (e.g. T1-weighted, T2-weighted, PD-weighted MR images) for the same subject as inputs, where the multi-contrast MR images acquired for a single subject, for the same anatomical structures such as the brain for example, contain underlying correlations in the structure and texture patterns visible in the images. Examples of the present disclosure learn the correlations existing across multi-contrast MR images for a given subject to learn a mapping (also referred to as transformation, or a way to convert) from the multi-contrast MR images of the subject to an MRA image specific to the same subject (referred to as synthesising an MRA image from multi-contrast MR images).

The motivation for the present disclosure is the desire to generate digital twin populations of cerebrovascular anatomy at scale (i.e. in large numbers, for example so that they are more statistically significant) for use in in-silico studies and/or ISTs. A reliable technique for synthesising MRA images (i.e. of one imaging modality) of a subject from other multi-contrast MR images (i.e. from other, different, modalities, but of the same subject), is valuable because: (i) there are few large databases with imaging modalities (such as MRA) that enable quantitative characterisation of whole-brain vasculature; and (ii) no large public database exists that provides image-derived geometries/ models of whole-brain vasculature, ready for use in studies investigating cerebrovascular haemodynamics. The largest public database of whole-brain vascular geometries/models is the BraVa database, which comprises just 61 samples of healthy adults. This paucity of data has thus limited the size of in-silico studies conducted thus far to assess cerebrovascular haemodynamics (in both healthy and pathological populations), and hence limited the degree of inter-patient variability that has been available to characterise and leverage to improve our understanding of the interplay between anatomy, physiology and pathological processes in the brain.

Generating or synthesising one type of MR image contrast (e.g. MRA) from other types of MR images (i.e. multi-contrast MR images) is also referred to as image-to-image translation or domain adaptation. It is the process of transforming one or more images in one or more domains (i.e. multiple domains in the present example refers to multi-contrast MR images) to one or more images in one or more different domains (i.e. in the present example, transforming multi-contrast MR images of a subject/patient to an MRA image of the same subject/patient). Image-to-image translation may be achieved using statistical or machine learning approaches, where the chosen statistical or machine learning model is initially trained on imaging data acquired for healthy subjects or patients with disease/abnormalities, to learn the mapping from the source domain for each patient (i.e. in the present example, this refers to the multi-contrast MR images for each patient) to the target domain for the same patient (i.e. in the present example, this refers to the MRA image for each patient). Following training of the statistical or machine learning model, given new patients' source domain images as input, previously unseen by the model, the model generates or synthesises the patients' corresponding target domain images. By training a statistical or machine learning model to learn the mapping/transformation from multi-contrast MR images of the brain for a given patient/subject, to an MRA image specific to that patient/subject, large scale (i.e. having 1000+ examples) databases of patient/subject-specific MRA images may be synthesised using the large-scale databases of multi-contrast MR images without paired MRA images, that are publicly available.

Examples of the present disclosure aims to facilitate the creation of such a large-scale, synthetic, subject-specific MRA imaging database of the brain, wherein, the synthesised MRA images preserve the structural and morphological properties of blood vessels in the brain, relative to those observed in native anatomy (i.e. as observed in real MRA images acquired for patients/subjects). Examples of the present disclosure also aim to enable the extraction and quantitative characterisation of patient-/subject-specific whole-brain vascular (also referred to as cerebrovascular) geometries/models in 3D using the synthesised MRA images, wherein, the extracted 3D vessel geometries from the synthesised images represent anatomically plausible representations of patient-/subject-specific cerebral vasculature (i.e. blood vessels in the brain). Synthesising patient-/subject-specific MRA images, and extraction of 3D cerebrovascular geometries/models therefrom, allows creation and curation of 'digital twin' cohorts of cerebrovascular geometries/models, for use in in-silico studies assessing cerebral haemodynamics and/or evaluating the performance of medical devices (or pharmaceuticals/medicines) used to treat abnormalities/pathologies/diseases in the brain, in-silico (i.e. are suited for use in ISTs of cerebral medical devices and medicines).

It is an object of the present disclosure to mitigate one or more of the problems set out above. The technology described herein provides an image-to-image translation framework (also referred to as a domain adaptation framework or multi-source-to-target image translation or multi-image-to-single-image translation framework) that enables synthesis/generation of patient-/subject-specific 3D brain MRA images, from patient-/subject-specific 3D brain multi-contrast MR images (such as T1-weighted, T2-weighted and PD-weighted MR images). The patient-/subject-specific MRA images synthesised/generated using the described technology may be segmented (meaning the outlining/contouring/delineation of structures of interest, namely, the blood vessels in the brain) using existing segmentation algorithms to extract anatomically plausible 3D whole-brain vascular (also referred to as cerebrovascular or blood vessels in the brain) geometries. Here anatomical plausibility means that the 3D whole-brain vascular geometries extracted from synthesised MR images, preserve/retain/are consistent with the structural and morphological properties observed in native anatomy of the same patients/subjects (i.e. relative the blood vessel geometries extracted from real MRA images acquired for the same patients/subjects). Additionally, examples of the present disclosure ensure that computational fluid dynamics (CFD) simulations of blood flow in the 3D whole-brain vascular geometries extracted from synthesised MRA images are consistent with CFD simulations of blood flow in 3D whole-brain vascular geometries extracted from real MRA images for the same patients/subjects (i.e. hae-modynamic characteristics are preserved).

Advantageously, the described technology and associated apparatuses allow any combination of the multi-contrast MR images to be used as the source domain images for training the system to generate/synthesise the target domain images, namely, the MRA images. The source domain images considered in the present disclosure are—T1-weighted, T2-weighted and PD-weighted MR images; and the target domain image is an MRA image. However, the general teachings herein may also be applied to other input and output domain types, according to some examples. A specific example according to the present disclosure is designed for 'paired' multi-image-to-single-image translation, meaning that given multi-contrast images for a specific patient/subject as input, the developed system is trained to learn a mapping to generate a corresponding MRA image for the same subject/patient. This is different to 'unpaired' multi-image-to-single-image translation (also referred to as unpaired domain adaptation), where, given multi-contrast images from one or several different patients, the goal is to synthesise a target domain image for a different patient, whose imaging data is not included in the inputs. In other words, 'paired' image translation refers to patient-/subject-specific image translation, while 'unpaired' image translation refers to cross-patient/subject image translation.

An example of the present disclosure that is for 'paired' multi-image-to-single image translation is focused on 3D multi-contrast brain MR images to 3D MRA translation, i.e. using 3D multi-contrast brain MR images as inputs to synthesise/generate 3D MRA images in a patient-/subject-specific manner. An example of the method is based on a deep Convolutional Neural Network (CNN), specifically, a conditional Generative Adversarial Network (cGAN). An example of the developed cGAN for synthesising patient-/subject-specific 3D MRA images from other multi-contrast 3D MR images comprises two modules/sub-networks referred to as the 'generator' and 'discriminator' sub-networks. The generator and discriminator sub-networks use the shared/correlated and complementary information available in the inputted 3D multi-contrast MR images to synthesise realistic/anatomically plausible patient-/subject-specific 3D MRA images. The generator and discriminator sub-networks in the specific example are 3D CNNs. 3D CNNs are used to learn relevant structural and texture information in 3D from the inputted multi-contrast MR images, to preserve cerebrovascular characteristics (i.e. structural and morphological properties of blood vessels in the brain) in the synthesised MRA images. The disclosed multi-image-to-single-image translation framework, based on a cGAN, for synthesising patient-/subject-specific MRA images from other multi-contrast MR images, is described by the schematic shown in FIG. 1, in the specific use-case of generating MRA images of the brain.

Compared with prior known technologies, the key unique and novel contributions of the present disclosure are—(i) the capability to synthesize patient-specific 3D MRA images of the brain, from inputted 3D T1, T2 and PD-weighted brain MR images in a manner that preserves continuity of vascular anatomy; (ii) use of a novel multi-view maximum intensity projection-based loss function to guide the synthesis of MRA images whilst preserving the structure of blood vessels; (iii) verification that vascular geometries extracted from synthesised brain MRA images preserve key morphological characteristics and blood flow-derived parameters or properties relative to vessel geometries extracted for the same patients from real brain MRA image acquisitions.

BRIEF DESCRIPTION OF THE DRAWINGS

Examples of the invention are further described hereinafter with reference to the accompanying drawings, in which:

FIG. 2 shows an example encoder network of a generator network architecture for use in the system of FIG. 1, according to an example of the disclosure;

FIG. 3 shows an example decoder network of a generator network architecture for use in the system of FIG. 1, according to an example of the disclosure;

FIG. 10 shows real life examples of the T1, T2 and PD-weighted images for 6 subjects, as well as the resultant associated synthesised MRA images and synthesised MRA (MIP) images;

DETAILED DESCRIPTION

The technical operation and advantages of the present disclosure shall now be provided by way of a plurality of examples that are merely illustrative of the novel and inventive features, and the disclosed examples are intended to be fully combinable in any reasonable combination.

Figure 1:
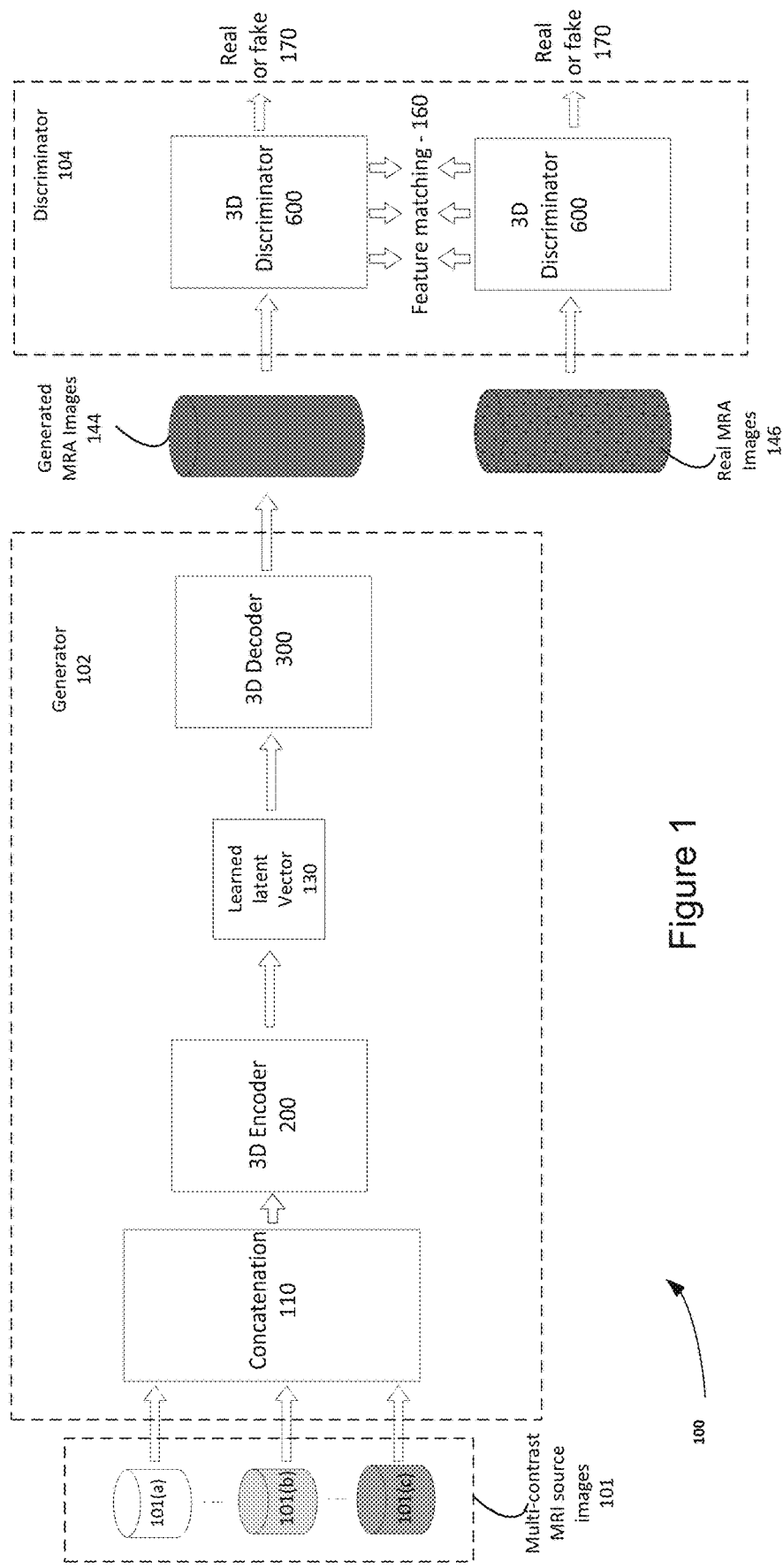
FIG. 1 shows an example system for generating individual-specific magnetic resonance angiography images from other inputted MR image contrasts, according to an example of the present disclosure.

FIG. 1 shows an example system for generating/synthesising patient-/subject-specific 3D MRA images according to an example of the disclosure, in general terms. The disclosed system provides an end to end generative adversarial network that can synthesise anatomically plausible, high resolution 3D MRA images using the most commonly acquired multi-contrast images (i.e. T1/T2/PD-weighted MR images) for the same subject, whilst preserving the continuity of the vascular anatomy. The disclosed system in its most generic form, which may also be referred to as an image-to-image translation or domain adaptation or multiimage-to-single-image translation system, is a type of conditional generative adversarial network (cGAN), which comprises two components/modules/sub-networks—a 'generator' module and a 'discriminator' module. The generator module comprises a pair of sub-networks referred to as the encoder and decoder networks. The encoder sub-network of the generator module takes as input one or more subject patients' source domain images (e.g. multi-contrast MR images such as any combination of T1-weighted, T2-weighted and PD-weighted MR images) and provides as output a low-dimensional representation of the inputted multi-contrast images, referred to as a latent vector (or feature vector or feature embedding). The decoder sub-network in the generator module takes as input the latent vector output by the encoder sub-network and maps/transforms this low-dimensional representation of the multi-contrast images inputted to the encoder sub-network, to their corresponding, patient-/subject-specific MRA image.

In the present disclosure, both the generator and discriminator modules are parameterised (i.e. defined by) by 3D convolutional neural networks (CNNs). A 'paired' image-to-image translation model, also referred to as a 'paired' domain adaptation model or a 'paired' multi-image-to-single image translation model, as used in the disclosed system, is an algorithm that can learn a shared/combined representation of multiple inputted images acquired from a specific patient/subject (i.e. can fuse information into a low-dimensional representation from inputted multi-contrast MR images such as T1-weighted, T2-weighted and PD-weighted MR images belonging to a specific patient/subject), and then transform/map this fused low-dimensional representation, referred to as a latent vector/feature embedding, into a target domain image specific to the same patient/subject (e.g. MRA image, in the present disclosure). The target domain image in the present disclosure and for this type of algorithm belongs to a different domain/contrast than the inputted images source domain images. Here, different domain/contrast refers to the different appearance/intensity distributions of the target and source domain images, and the difference in the material properties/soft tissue characteristics (of the imaged object/region) that their respective acquired signals are sensitive to. The 'paired' multi-image-to-single-image translation model is used for synthesising/generating patient-/subject-specific MRA images, given a specific patient/subject's multi-contrast MR images as input. In the following example disclosure, the example used will be the synthesis of a human patient/subject's brain 3D MRA image, given a specific patient/subject's 3D brain multi-contrast MR images as input, including any combination of the following MR contrasts as inputs—T1-weighted, T2-weighted and PD-weighted MR images. In some examples, the importance assessments of the resultant generated images indicates that the T2 and PD-weighted images may be better predictors of MRA images than T1, and the PD weighted images may contribute to better visibility of small vessel branches towards the peripheral regions. The disclosed system is however, generic and may be used to synthesise other target contrast MR images of the brain, given any combination of the above mentioned multi-contrast MR images as inputs.

The disclosed system for 'paired' multi-image-to-single image translation framework is implemented as a conditional generative adversarial network (cGAN). 'Paired' image translation models learn to map a set of N observed source domain images denoted $I=\{I_n\}_{n=1 \ldots N}$ to a statistically dependent target domain image y. A generative adversarial network (GAN) is a type of generative model that can be trained to learn the distribution of some inputted training data and, following training, can be used to synthesise new data/instances of data that are realistic, and similar but not identical to instances in the training dataset. A GAN and its conditional variant, cGAN, both comprise two modules or sub-networks, typically referred to as the generator and discriminator. The generator (G) and discriminator (D) modules compete against each other during training, with G trying to learn the training data distribution to synthesise realistic but fake examples of the real/training data, and D trying to differentiate correctly between the fake synthetic data instances synthesised by G and the real data instances observed in the training dataset. In other words, to train a GAN given some training data, G and D compete in a minimax (also referred to as zero-sum) game to find the Nash equilibrium between the two modules. In a GAN, G learns to map/transform an inputted random noise vector z (may be a random noise vector sampled from a Gaussian distribution or other similar probability distributions) to an output image y, where y is an instance of the training data distribution (i.e. $G(z)=y$ represents the transformation/mapping learned by G to transform randomly sampled vectors from some chosen distribution, such as a Gaussian for example, to the training data distribution).

FIG. 1 shows an example system that provides an end to end generative adversarial network 100 according to the present disclosure. The system 100 has as inputs a plurality of multi-contrast, different modality, image inputs 101, such as MRI source images from T1 101(a), T2 101(b) and PD-weighted 101(c) image sets. These are fed into the Generator 102, which may first concatenate the different images sets together using a concatenator 110. The concatenated images may then be fed into the encoder (in this case, 3D encoder 200, of FIG. 2), to produce a learned latent vector 130, which, in turn, is then fed into the decoder (in this case 3D decoder 300, of FIG. 3), to produce generated/synthesized MRA images 144. In some other examples, there may be no concatenation, and instead there is a separate encoder per input image data set.

Meanwhile, the overall system also includes a Discriminator, D, 104, this in this example comprises two separate 3D Discriminators 600 (which have the same architectures, and share parameters, but operate on different source images), with one operating on the generated MRA images 144, and the other operating on the real example MRA images 146, respectively, and working together to provide a feature mapping output 160, and decision output 170 on whether the images are real or fake, as will be described in more detail below.

During the training stage, the Generator 102 and Discriminator 104 are trained in alternating periods. That is, the Generator 102 trains for one epoch, and then the Discriminator 104 trains for one epoch. The Generator 102 is kept constant during the Discriminator 104 training phase. Similarly, the Discriminator 104 is kept constant during the Generator 102 training phase. These two steps (i.e. Generator 102 and Discriminator 104) may be repeated, alternatingly, to continue to train the Generator 102 and Discriminator 104 networks accordingly. During the inference stage, the Discriminator 104 cycle may be discarded and only the Generator 102 may be used to conditionally synthesise MRA images, given other MR-contrast images as inputs, in one forward pass.

In the cGAN developed for paired multi-image-to-single image translation or single-image-to-single image translation according to the present disclosure, an encoder network (for example, as shown in FIG. 1) is used to learn a transformation/mapping from multiple or single inputted images, respectively, to a latent vector/feature embedding z, which in turn is inputted to the Generator, G, 102. In other words, the generative process in a cGAN is conditioned on some information derived from the provided image inputs (101(a)-101(c)) and is expressed as $G(z|I_1, I_2, \ldots I_N)=y$, where, $I_1, I_2, \ldots I_N$ represent the N images inputted to the encoder network 100, that act as conditioning variables/information for the generative process. In both GANs and cGANs, during training, G 102 generates/synthesises fake images 144 which are passed as inputs to Discriminator, D, 104. D 104 also receives real images 146 from the training dataset as inputs and D 104 is trained to classify/differentiate between the inputted images as being real or fake 170 (where, fake refers to being images synthesised by G 102). Both G 102 and D 104 are trained together using a loss function that encourages G 102 and D 104 to compete against each other (also referred to as an adversarial loss function), where G 102 tries to fool D 104 by synthesising images that appear increasingly realistic as training progresses, while D 104 tries to correctly differentiate between real and fake images. The adversarial loss function ($L_{cGAN}$) used to optimise and train G 102 and D 104 in a cGAN is given by:

$$\mathcal{L}_{cGAN}(G, D) = \mathbb{E}_{I_N, y}[\log D(I_n, y)] + \mathbb{E}_{I_n}[\log(1 - D(I_n, G(I_n)))] \quad (1)$$

Where, $\mathbb{E}$ represents the expectation; $I_n$, for $n=1 \ldots N$ represents the concatenated/combined source domain images inputted to the encoder network 100; and y represents the target domain image that the Generator 102 tries to synthesise, conditioned on the inputs 101(a)-(c). Previous methods for single-image-to-single-image translation or multi-image-to-single-image translation using cGANs have also combined a reconstruction loss term with the adversarial loss function $\mathcal{L}_{cGAN}(G, D)$ to encourage the Generator network G 102 to synthesise images that are visually closer to the target domain images of interest. Typically, the reconstruction loss term is formulated as the Euclidean (L2) distance or the L1-norm distance between the synthesised images 144 outputted by G 102 and their corresponding target domain images y. The resulting overall loss function to train a cGAN for paired multi-image-to-single-image translation is given by:

$$\mathcal{L}_{overall} = \mathcal{L}_{cGAN}(G, D) + \mathcal{L}_{recon} \quad (2)$$

Where the reconstruction loss, $\mathcal{L}_{recon}$ may be formulated as:

$$\mathcal{L}_{recon} = \mathbb{E}_{I_N, y}[\|y - G(I_n)\|_1] \text{ or } \mathcal{L}_{recon} = \mathbb{E}_{I_N, y}[\|y - G(I_n)\|_2] \quad (3)$$

According to an example of the present disclosure, the source domain images may comprise N=3 different brain MR images for each patient, namely, T1-weighted, T2-weighted and PD-weighted MR images; and the target domain image is the corresponding brain MRA image for each patient. The above-described conventional reconstruction loss of Equation (3) may be modified, in order to ensure that blood vessels visible in the target domain MRA images, and are suitably recovered in the synthesised MRA images outputted by the Generator network 102 according to the present disclosure. The modified reconstruction loss term developed in the disclosed system is described in subsequent paragraphs. Additionally, in the disclosed system, the conventional adversarial loss function of Equation (1) may be modified to utilise the least squares (L2) loss function given by:

$$\mathcal{L}_{cGAN}(G, D) = -\mathbb{E}_{I_N, y}\left[(D(I_n, y) - 1)^2\right] - \mathbb{E}_{I_N}\left[D(I_n, G(I_n))^2\right] \qquad (4)$$

Note, the above equation is negative, since it is trying to minimise the least squares loss, as opposed to maximising the log-likelihood as per equation (1).

FIG. 2 shows an example encoder network of a Generator network architecture for use in the system of FIG. 1, according to an example of the disclosure. The source domain images are inputted to the encoder 200 sub-network in G 102, concatenated 110 into a tensor 201 (i.e. a type of machine learning data structure used in linear algebra, and like vectors and matrices, on which you can calculate arithmetic operations) and features (in the form of features maps 202-205, which are the inputs/outputs of the respective generator convolution blocks 210-240, see next) are extracted through a sequence of four generator convolution blocks 210-240. Each generator convolution block in the encoder sub-network is made up of a 3D strided convolution layer (e.g. item 212 within first convolution block 210, item 222 in second convolution block 220, etc), a 3D instance normalisation layer (e.g. 214, within first generator convolution block 210, etc), followed by a leaky rectified linear unit (LeakyReLU) activation layer (e.g. 216, within first generator convolution block 210, etc). Note, the same general reference numeral labelling methodology is used in the drawings, so there is a similar but differently labelled instance of each type of sub unit (e.g. 212, 222, 232, etc, or 214, 224, 234, etc,) in each greater generator convolutional block/unit (e.g. 210, 220, 230, etc). This is to show the different sub-units are typically the same, or at least very similar, architecture(s), but with different operational and/or set up parameters in use. For example, 3D convolution 212 of block 210 is similar to, but differently set up, to the 3D convolution 222 of block 220.

Strided convolution layers 212,222,232,242 are responsible for learning features relevant to the learning task and down-sampling the inputs. The down-sampling factor is controlled by stride size, and, according to one example, a stride of 2×2×2 is used in all convolution blocks in the encoder 200 sub-network of the disclosed system. Other stride values (esp. higher stride values) may be used in alternative implementations, with the different stride values possibly being derived empirically. Normalisation layers ensure that learned features with diverse magnitudes/ranges have proportional impact or importance on network predictions. In the example of FIG. 2, Instance normalisation layers 214, 224, 234, 244 are used in particular, where this type of normalisation operates on each individual sample or input provided to the layer and spatially normalises the contrast of each input. In other words, given an input image, instance normalisation performs intensity normalisation across the width and height of each feature map in each inputted sample. Features maps 202-204 are passed between the convolution blocks ultimately resulting in end features map 205 that is extracted by the sequence of convolution blocks 210-240 in the encoder sub-network, and this is passed to a fully connected or dense layer 250, which in turn outputs a latent vector 130 or embedding of the source domain images, used as conditioning information for the conditional synthesis of, in this example 3D, MRA images produced by the cGAN in the developed system. Details of the encoder sub-network architecture are provided in Table 1.

TABLE 1

An example architecture for the encoder and decoder sub-networks in the Generator (G) of the cGAN used in the disclosed system.

| Encoder | Decoder |
|---|---|
| Input: Multi-contrast 3D MR source domain images ($I_n$) | Input: Latent vector ($z_i$) |
| Strided Convolution Downsampling Blocks 1-4 (Convolution kernel size: (3 × 3 × 3), padding: (1 × 1 × 1), stride: (2 × 2 × 2)). | Residual Convolution Up-sampling Blocks 1-4 |
| Fully connected output layer (size: (512 × 1)) | 1 × 3D Convolution Layer (Convolution kernel size: (3 × 3 × 3) padding: (1 × 1 × 1), stride: (1 × 1 × 1) Tanh activation layer |
| Output: Latent vector ($z_i$) (size: (512 × 1)) | Output: Synthesised MRA image $G(I_n)$ |

The latent vector 130 outputted by the encoder 200 sub-network of the Generator 102 contains combined and condensed information from the source domain images inputted to the encoder 200. The outputted latent vector 130 is provided as input to the decoder 300 sub-network of G 102 in the disclosed adversarial system 100 of FIG. 1.

FIG. 3 shows an example decoder network of a Generator 102 network architecture for use in the system of FIG. 1, according to an example of the disclosure. The decoder 300 sub-network comprises a sequence of four up-sampling residual convolution blocks 310-340, taking as input a (reshaped) feature map 305 derived from the latent vector 130 (i.e. the latent vector output from FIG. 2) by reshaping 302 the latent vector into a square (N×N) feature map. Each residual convolution block 310-340 is made up of a residual block (ResBlock) 400-403, and up-sampling block 311-314. Again the numbering used in the figure is to try to show how the basic architecture is the same, but there are specific and differently set up instances (for example, of ResBlock of FIG. 4, there are instances 400 to 403, and for the up-sampling block, there are instances 311 to 314, within residual convolutional block 310 to 340, respectively).

Final 3D convolution layer 350 is the last 3D convolutional layer added to the decoder, followed by a Tanh Activation layer 360, which operates to ensure that the output images are normalized to be in the range [−1, 1]. The final output 144 comprises the final resultant generated MRA images.

Figures 4, 5:
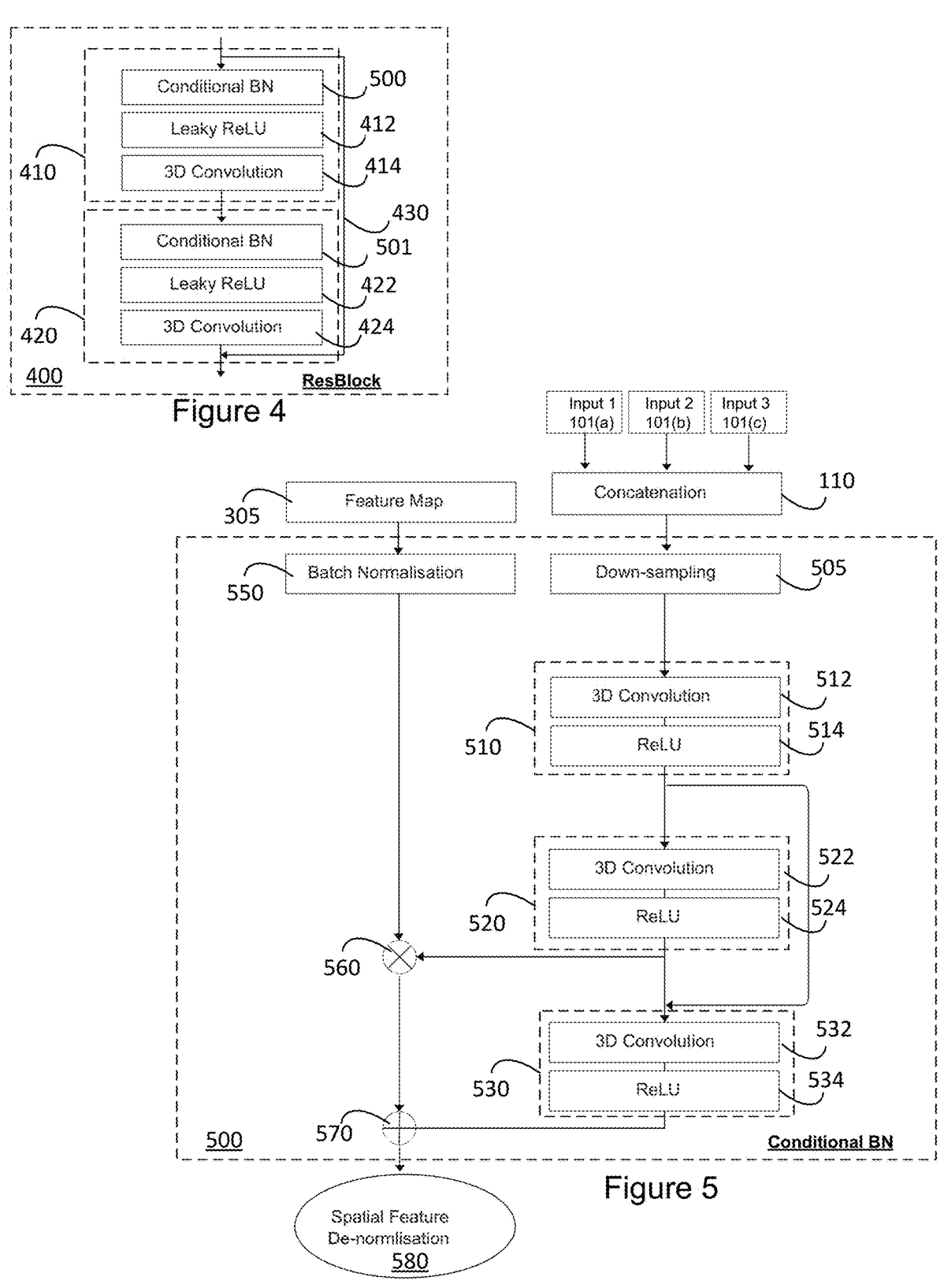
FIG. 4 shows an example residual block (ResBlock) architecture for use in the decoder of FIG. 3, according to an example of the disclosure.
FIG. 5 shows an example conditional batch normalisation (CBN) architecture for use in the ResBlock of FIG. 4, according to an example of the disclosure.

FIG. 4 shows an example residual block (ResBlock) 400 architecture for use in the decoder of FIG. 3, according to an example of the disclosure. Each of the other ResBlocks 401-403 is of the same architecture as Resblock 400. ResBlock 400 is made up of a sequence of two sub-blocks, 410 and 420, each called a CBN-LeakyReLU-Conv sub-block. Each CBN-LeakyReLU-Conv sub-block comprises a conditional batch normalisation (CBN) layer 500 (labelled 501 for the second instance), a leaky rectified linear unit activation (LeakyReLU) layer 412/422 and a 3D convolution (Conv) layer 414/424, in that order. Note, the Leaky ReLU blocks 412/422 are the same functions as the Leaky ReLU functions 216/226/etc, as shown in FIG. 2, but being applied to different data inputs in this FIG. 4. All 3D convolution blocks within the conditional batch normalisation layers (500) and the residual blocks (400) are identical convolution operations with the same kernel, padding and stride used throughout the decoder (as specified in Table 1). There is also a bypass 430, where a learned residue of the input is added to the output to ensure the characteristics of original images are retained.

FIG. 5 shows an example conditional batch normalisation architecture for use in the ResBlocks 400-403 of FIG. 4, according to an example of the disclosure.

Reverting briefly to FIG. 4, the CBN layers 500/501 enable conditioning information (i.e. information derived from the input images 101(a)-101(c), as noted above) to be incorporated into the conditional image generation process, and for the normalisation of inputted feature maps to be normalised whilst accounting for this additional conditioning information. This ensures that shared structural details across conditioning information provided as inputs to the CBN layer 500/501, are propagated effectively through the Decoder 104 and are used to conditionally normalise the inputted feature map (305) obtained as output from the encoder of G 102 (in the case of the first CBN layer in the decoder) or as output from the preceding CBN-LeakyReLU-Conv block in the decoder (items 304-302).

As shown in FIG. 5, the input multi-contrast structural MR images sets 101(a)-(c) used as the source domain (T1-weighted, T2-weighted and/or PD-weighted images, respectively) are concatenated 110, before down-sampling 505, and then used as conditioning information inputs to the CBN layers 500/501 (refer to FIG. 4). The inputted feature maps (305) to each CBN layer 500 are first batch normalised to zero mean and unit standard deviation (550) and then normalised features are subsequently modulated/de-normalised using an affine transformation whose scale is derived from an element wise multiplication operation (560) and shift parameters are derived from an element wise addition operation (570), which are learned from the provided conditioning inputs (coming out from the concatenation function 110) to the CBN layers. i.e. in the disclosed system, the multi-channel input comprising concatenated multi-contrast MR images (110) learned through a CNN (512, 514, 522, 524, 532, 534) are used to modulate the normalised feature maps. The final de-normalised feature maps are denoted as the item Spatial Feature De-normalisation 580.

The overall conditional batch normalisation process can be described as follows: first the inputted batch of feature maps to the CBN layers 500/501, denoted, $n_{b,w,h,c} \in \mathbb{R}^{B \times W \times H \times C}$ (where, $b \in B$, $w \in W$, $h \in H$ and $c \in C$ represent the batch size, width, height and number of channels of the inputted feature maps, respectively) are normalised channel-wise (i.e. using output 580). This channel-wise normalisation is given by:

$$n'_{b,w,h,c} = \gamma_{w,h,c}(I_n) \times \frac{n_{b,w,h,c} - \mu_c}{\sigma_c + \varepsilon} + \beta_{w,h,c}(I_n) \qquad (5)$$

where, $\mu_c = 1/N\Sigma_{b,w,h} n_{b,w,h,c}$ and $\sigma_c^2 = 1/N\Sigma_{b,w,h}(n_{b,w,h,c} - \mu_c)^2$. As before, $I_n$ denotes the multi-channel inputs comprising the source domain multi-contrast MR images; $\gamma(\bullet)$ and $\beta(\bullet)$ represent the spatial dimension-dependent functions, also referred to as CBN modulation parameters, $\mu_c$ and $\sigma_c^2$ represent the mean and variance of the inputted batch of feature maps $n_{b,w,h,c}$ which are used to normalise the batch of feature maps to zero mean and unit standard deviation, resulting in a batch normalised feature maps $n'_{b,w,h,c}$ and $\varepsilon$ denotes a small constant value included to prevent division by zero. According to one example, $\gamma(\bullet)$ and $\beta(\bullet)$ were parameterised as 3D convolution kernels of kernel size: (3×3×3), padding: (1×1×1) and stride: (1×1×1), and were learned together with the CBN modulation parameters $\gamma(\bullet)$ and $\beta(\bullet)$, during training of the cGAN. The final outputs from the 3D decoder sub-network 300 in G 102 (as shown in the FIG. 3) are the synthesised/generated MRA images 144.

As will now be appreciated by the skilled person, the Generator 102 is an encoder-decoder model, where the encoder aims to extract the features of the source images, and the decoder maps the underlying representation into MRA images.

The outputs of the Generator G 102, namely, the synthesised MRA images 144, are in turn inputted to the Discriminator (D) network 104, which will now be explained with reference to FIGS. 6 and 7. The role of the Discriminator in a GAN or a cGAN is to distinguish the synthesised images 144 outputted by the Generator network (G) from their real image counterparts 146. In the disclosed system, the role of the Discriminator, D, 104 is to distinguish between synthesised subject-specific MRA images and the real MRA images specific to the same subject. By training the networks G and D jointly through the adversarial loss, as the performance of D improves, it forces G to synthesise more realistic images, in an attempt to fool D. Thus, the adversarial methodology of the system according to the present disclosure leads to the synthesis of more realistic MRA images that preserve key morphological characteristics of blood vessels, visible in the MRA images.

Figures 6, 7:
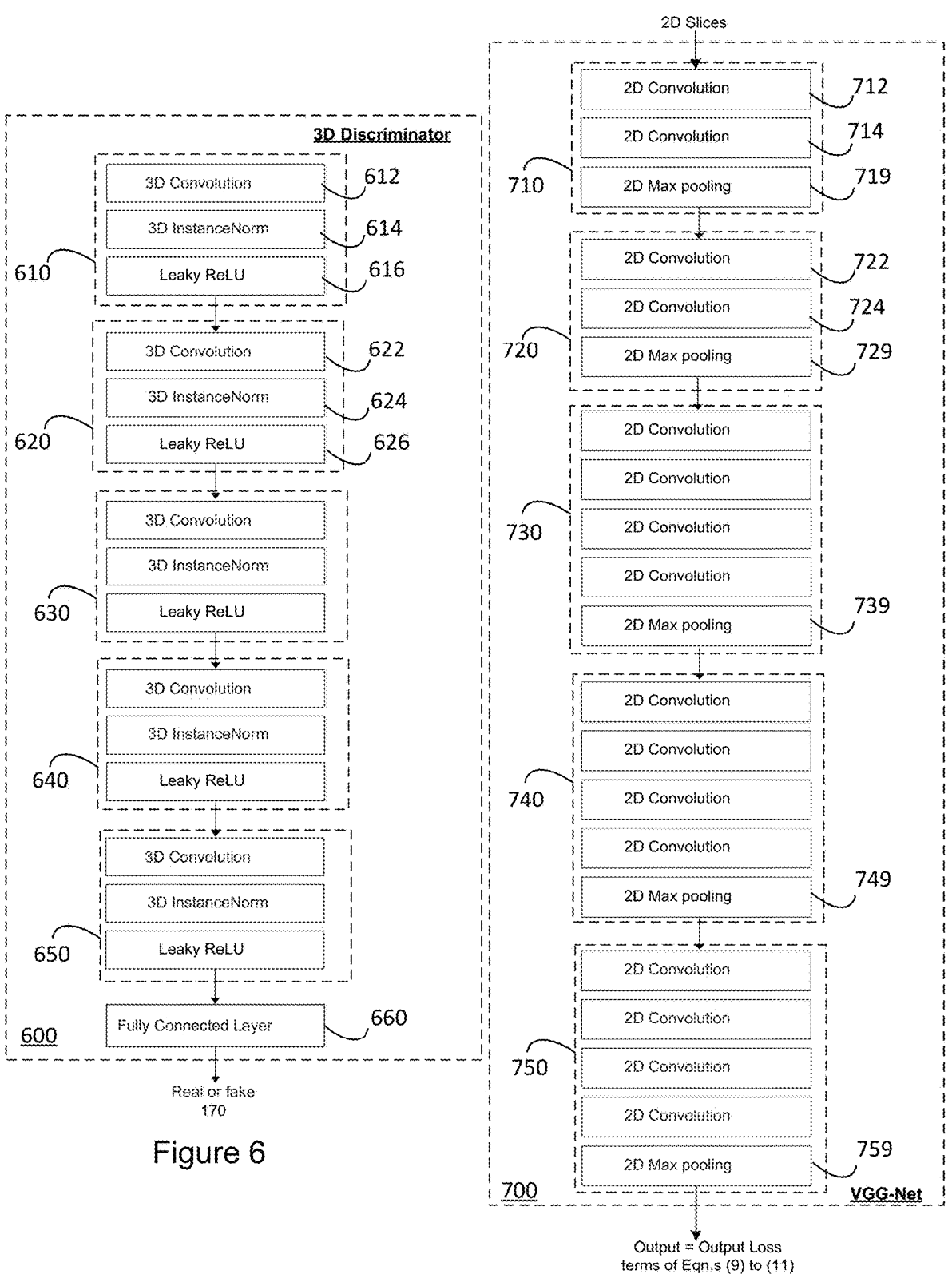
FIG. 6 shows an example architecture of a 3D discriminator network for use in the system of FIG. 1, according to an example of the disclosure.
FIG. 7 shows an example VGG network for use in the system of FIG. 8, according to an example of the disclosure.

FIG. 6 shows an example architecture of a 3D Discriminator network 600 for use in the system of FIG. 1, according to an example of the disclosure (where there is one of these per scale/resolution path). The example 3D Discriminator network 600 used in the disclosed system is implemented as a multi-scale pyramid network, operating across two spatial scales/resolutions. Implementing the Discriminator 104 as a multi-scale network helps improve the recovery of global and localised structural information in the synthesised images. The multi-scale 3D Discriminator refers to multiple instances of the network (600) shown in FIG. 6, operating at different spatial scales. The Discriminator 104 thus has two sub-networks 600, one operating at the original spatial scale/resolution of the image data and the second operating at a lower spatial scale/resolution (see FIG. 9, of the whole system in use, with example image data). The real images 146 and the synthesised images 144 (outputted by G) are thus down-sampled (e.g. by a factor of 2 in this example, but this step is not shown in the Figures—it is effectively provided by the stride used) and inputted to the low-resolution sub-network of D 104 (i.e. a first instance of FIG. 6), while the images in their original/native spatial scale/resolution are inputted to the higher resolution sub-network of D 104 (i.e. a second instance of FIG. 6). The two sub-networks 600 in D 104 are trained jointly. Training of D 104 means that the individual loss functions specific to each of the constituent sub-networks 600 of D 104, are combined and minimised jointly. The sub-network 600 of D 104 operating at a lower spatial scale/resolution has a large receptive field size, allowing it to learn more global features, while the other sub-network, operating at a higher spatial scale/resolution, captures local structural information due to its small receptive field size. Each sub-network 600 in D (refer to FIG. 6) comprises five convolution blocks 610-650, with each block comprising a 3D convolution layer 612, 622, etc, an instance normalisation layer 614, 624, etc and a LeakyReLU activation layer 616, 626, etc., ending up with a final fully connected layer output 660. All 3D convolution blocks, 3D InstanceNorm blocks and Leaky ReLU blocks are operationally similar to those in FIG. 5, but with different parameters set(s), as per the discrimination operation involved. Details of an example network architecture for each sub-network in D are provided in Table 2.

TABLE 2

| Discriminator sub-network 1: Higher spatial scale/resolution | Discriminator sub-network 2: Lower spatial scale/resolution |
|---|---|
| Input: Real and synthesised MRA image in native/original image resolution (Input size: 256 × 256 × 32) | Input: Downsampled (×2) real and synthesised MRA image (Input size: 128 × 128 × 32) |
| Strided Convolution Blocks 1-5 (Convolution kernel size: (4 × 4 × 4), padding: (2 × 2 × 2), stride: (2 × 2 × 2)). | Strided Convolution Blocks 1-5 (Convolution kernel size: (4 × 4 × 4), padding: (2 × 2 × 2), stride: (2 × 2 × 2)). |
| Instance Normalisation layer | Instance Normalisation layer |
| LeakyReLU activation layer (slope: 0.2) | LeakyReLU activation layer (slope: 0.2) |
| Fully connected layer (size: (N × 1) | Fully connected layer (size: (N × 1) |
| Output: (1 × 1) predicted label of whether inputted image is real or synthesised | Output: (1 × 1) predicted label of whether inputted image is real or synthesised |

The exemplary multi-scale Discriminator D 104 comprising two sub-networks operating at a higher and lower spatial scale/resolution, respectively, is trained using a modified version of the least-squares adversarial loss function given by:

$$\mathcal{L}_{cGAN}(G, D_k) = -\mathbb{E}_{I_N,y}[(D_k(I_n, y) - 1)^2] - \mathbb{E}_{I_N}[D_k(I_n, G(I_n))^2] \quad (6)$$

where, $k \in [1,2]$ denotes the multi-scale Discriminator operating at two different scales.

The overall system (refer to FIG. 1) is trained by minimising an overall loss function comprising the least-squares adversarial loss function $\mathcal{L}_{cGAN}(G, D_k)$ of Eq. 6 above, and a reconstruction loss term $\mathcal{L}_{recon}$ of Eq. (3) above. Conventional reconstruction loss terms based on the L2- or L1-distance, evaluated between the target domain images (i.e. real images 146) and their synthesised counterparts (i.e. images 144, outputted by G 102), are replaced in the disclosed system with MRA domain-specific loss terms that act on the maximum intensity projection images along the 3 different axes, i.e. equations (9)-(11) below, that encourage the Generator network G 102 (refer to FIGS. 4 and 5) to preserve details of blood vessels in the synthesised MRA images, as visible in their corresponding (targets) real MRA images. The reconstruction loss implemented in the disclosed system operates across two domains, namely, on a first domain comprising the original/real 3D MRA image volumes and their synthesised counterparts outputted by G, and on a second domain of the 2D projections along three orthogonal directions (axial, sagittal and coronal) of the real and synthesised MRA images, as shown in FIG. 8.

Figure 8:
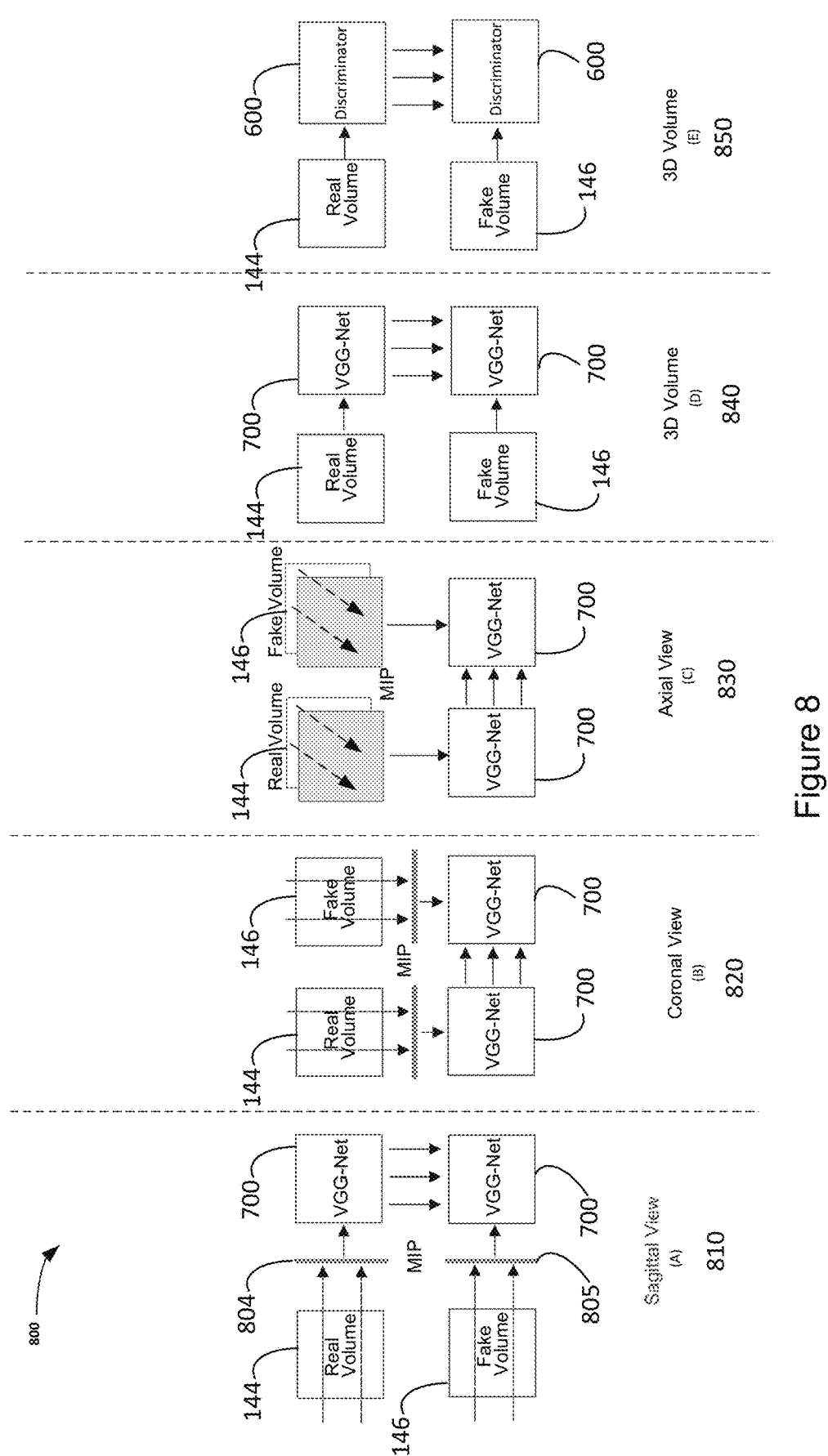
FIG. 8 shows an example implementation of the loss function used to train the system of FIG. 1, according to an example of the disclosure.

In brief summary, FIG. 8 shows the perceptual loss and measured perceptual differences between real and generated images in both 2D projection domain (left 3=(A) Sagittal View 810, (B) Coronal View 820 and (C) Axial View 830), and the 3D Volume domain (right most two—a first 3D volume (D) 840 and a second 3D volume (E) 850. As can be seen in FIG. 8, VGG-Nets (see FIG. 7) are used for the 2D domains 810-830, as well as the first 3D volume (D) 840, in each case through using high-level features extracted from a respective pre-trained VGG-Net. Meanwhile, for the second 3D volume (E) 850, the feature matching loss is based on the 3D Discriminator 600 and used to match the feature consistency between real data and synthesised data.

To explain FIG. 8 in more detail, the 2D projection images used along the axial 810, sagittal 820 and coronal 830 directions are known as maximum intensity projections (MIP—represented by plane lines 804/805—also see FIG. 10, bottom row), which highlight blood vessels and improve the contrast of vascular structures relative to background tissues. MIP images along orthogonal directions, namely, axial, coronal and sagittal are estimated by projecting the largest voxel values in the 3D MRA images along the corresponding orthogonal projection paths on to orthogonal 2D image planes. The reconstruction loss is formulated as a combination of a feature matching loss term operating on the 3D MRA image (i.e. first) domain and perceptual loss terms operating on both the 3D MRA image/first domain and the orthogonal 2D MIP image (i.e. second) domains. See FIG. 10 for examples of these images, as well as the respective input images. The feature matching loss $\mathcal{L}_{FM3D}$ (as used in item 850 in FIG. 8) minimises the difference in feature representations at intermediate layers of the multi-scale Discriminator network $D_k$ and is formulated as:

$$\mathcal{L}_{FM3D}(G, D_k) = \mathbb{E}_{I_N,y} \sum_{l=1}^{L} \frac{1}{N_l} [\|D_k^i(I_n, y) - D_k^i(I_n, G(I_n))\|_1], \quad (7)$$

where, $l=1 \ldots L$ represents the $l^{th}$ layer features in the multi-scale Discriminator $D_k$; $N_l$ is the number of features in each layer; and L represents the total number of layers in $D_k$. The perceptual loss terms operating over both the 3D MRA image/first domain and the 2D MIP image/second domains are used to measure perceptual differences between the real/original images 144 and the synthesised images 146 in both the 3D image domain and the 2D projection image domains. The perceptual loss terms are formulated as feature matching loss terms, using high-level features extracted from forward propagating the real and synthesised images through a pre-trained VGG-16 convolutional neural network, denoted V. The network architecture and layers from V used in the disclosed system is shown in FIG. 7.

FIG. 7 shows an example VGG-Net used in the present disclosure. The disclosed VGG-Net 700 comprises a plurality of VGG-Net convolution blocks (710-750), where the difference between them is related to the spatial scale involved, and where each convolution block includes a plurality of 2D convolution blocks (712, 714, etc), and a final 2D Max pooling block (719, 729-759). This VGG-Net is an architecture known to the skilled person, so will not be explained in more detail herein.

Reverting back to FIG. 8, the corresponding perceptual loss terms in the 3D/first domain 840 and the 2D projection/second domains along the axial, sagittal and coronal directions 810-830 are given by:

$$\mathcal{L}_{PER3D}(G, V) = \mathbb{E}_{I_N,y} \sum_{f=1}^{F} \frac{1}{M_f} [\|V^f(y) - V^f(G(I_n))\|_1], \quad (8)$$

$$\mathcal{L}_{PER2D-axial}(G, V) = \mathbb{E}_{I_N,y} \sum_{f=1}^{F} \frac{1}{M_f} [\|V^f(p_{axial}(y)) - \quad (9)$$

$$V^f(p_{axial}(G(I_n)))\|_1],$$

-continued $$\mathcal{L}_{PER2D-coronal}(G, V) = \mathbb{E}_{I_N, y} \sum_{f=1}^{F} \frac{1}{M_f} [\|V^f(P_{coronal}(y)) - \qquad (10)$$

$$V^f(p_{coronal}(G(I_n)))\|_1],$$

$$\mathcal{L}_{PER2D-sagittal}(G, V) = \mathbb{E}_{I_N, y} \sum_{f=1}^{F} \frac{1}{M_f} [\|V^f(p_{sagittal}(y)) - \qquad (11)$$

$$V^f(p_{sagittal}(G(I_n)))\|_1],$$

where, f=1 . . . F, denotes the features of f$^{th}$ layer of the pre-trained VGG-16 network resulting from forward passing: the real or synthesised 3D MRA images for $\mathcal{L}_{PER3D}$ (as used in item 840 in FIG. 8); the real or synthesised axial MIP images for $\mathcal{L}_{PER2D-axial}(G, V)$ (as used in item 830 in FIG. 8); the real or synthesised coronal MIP images for $\mathcal{L}_{PER2D-coronal}(G, V)$ (as used in item 820 in FIG. 8); and the real or synthesised sagittal MIP images for $\mathcal{L}_{PER2D-sagittal}(G, V)$ (as used in item 810 in FIG. 8). $M_f$ and F denote the number of features in layer f and the total number of feature extraction layers in V, respectively. The feature matching loss term and the perceptual loss terms are combined to formulate the reconstruction loss $\mathcal{L}_{recon}$ as:

$$\mathcal{L}_{recon} = \lambda_1 \left[\sum_{k=1}^{2} \mathcal{L}_{FM3D}(G, D_k)\right] + \lambda_2 \mathcal{L}_{PER3D}(G, V) + \qquad (12)$$

$$\lambda_3 \mathcal{L}_{PER2D-axial}(G, V) + \lambda_4 \mathcal{L}_{PER2D-coronal}(G, V) +$$

$$\lambda_5 \mathcal{L}_{PER2D-sagittal}(G, V)$$

where, $\lambda_1$, $\lambda_2$, $\lambda_3$, $\lambda_4$ and $\lambda_5$ represent weights that control the influence of each feature matching or perceptual loss term in $\mathcal{L}_{recon}$ on the overall learning process of the disclosed system. The complete loss function used to train the cGAN in the disclosed system in an end-to-end fashion is given by:

$$\mathcal{L}_{complete} = \min_{G} \left[\left[\max_{D1,D2} \sum_{k=1}^{2} \mathcal{L}_{cGAN}(G, D_k)\right] + \mathcal{L}_{recon}\right] \qquad (13)$$

where, $\mathcal{L}_{cGAN}(G, D_k)$ is the least-squares adversarial loss function expressed in Eq. (6) in the present disclosure. The loss term weights $\lambda_{1-5}$ are hyperparameters that are typically tuned empirically. The overall process of computing the perceptual loss terms defined in Eq. 8-11 is illustrated in FIG. 8. 3D MRA image volumes comprise several 2D slices that are stacked together and can be parsed along distinct dimensions or axes, these are specifically referred to as the axial, sagittal and coronal axes. Thus to compute the perceptual loss terms, the MIP of real and synthesised 3D MRA volumes is first computed and then the perceptual loss is evaluated along each of the above-mentioned axes. The above described loss functions are the multi-view maximum intensity projection-based loss function(s) noted as a key part of the disclosure.

Figure 9:
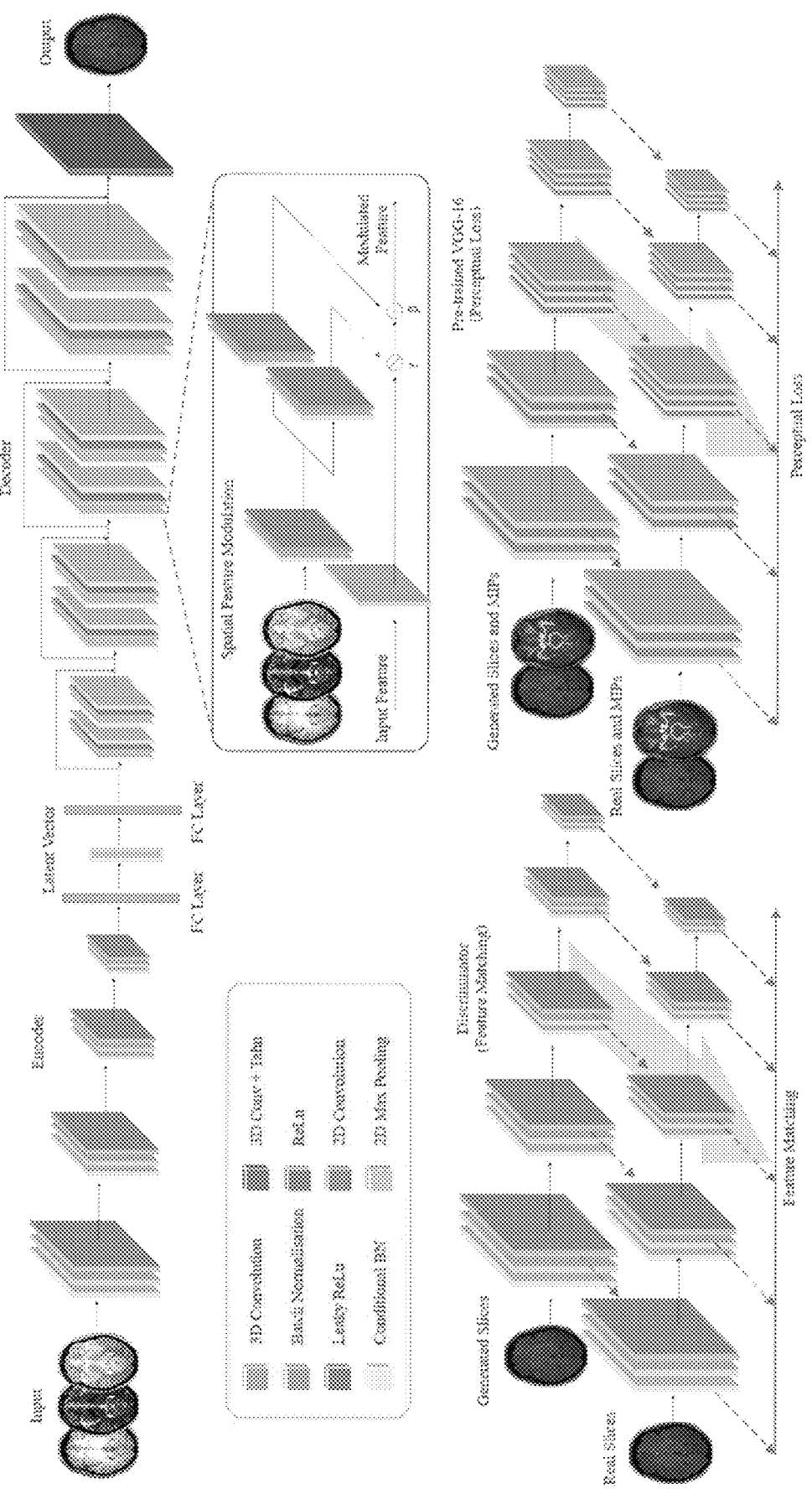
FIG. 9 shows a combined view of the overall system, according to an example of the disclosure.

FIG. 9 shows a combined view of the above-described overall system.

FIG. 10 shows real life examples of the acquired T1, T2 and PD-weighted structural MRI images for 6 subjects that may be used by an example of the present disclosure (and which are usually available in the public datasets), as well as the resultant corresponding synthesised MRA images (i.e. the MRA images that were not otherwise available in the datasets used), as well as the synthesised MRA (MIP)

images derived from the MRA images. This demonstrates that the proposed system, method and apparatuses can serve as an image imputation for missing/corrupted MRA images to prevent partially acquired subject data (sets) from being entirely discarded when analysing any given cohort of patients during an in-silico trial.

As noted above, the overall cGAN in the disclosed system may be trained to synthesise target 3D MRA images given multi-contrast 3D MR images as inputs such as T1-weighted, T2-weighted and PD-weighted images, in a subject-specific manner. This is to say that given multi-contrast MR images of a specific subject/individual as inputs and a target MRA image of the same subject, the cGAN in the disclosed system can be trained to synthesise an MRA image that resembles the target MRA image for that specific subject as closely as possible. Once the disclosed system is trained, it may be used to synthesise MRA images given just the multi-contrast MR images (such as T1-weighted, T2-weighted and PD-weighted images) as inputs to the system, thus is able to avoid the need to scan patients by each of the different modalities (which can save time, scanning resources, patient discomfort, and reduce exposure to potentially harmful accumulative scans, but also allows use of previously made scans which missed the specific modality at the time of scanning).

An example of the disclosed system was trained and tested on three separate brain MR imaging data sets, namely, IXI (http://brain-development.org/ixi-dataset/), MIDAS (http://insight-journal.org/midas/community/view/21/) and SIMONS (tp://fcon1000.projects.nitrc.org/indi/retro/SIMON.html). The disclosed system was designed and developed for the task of synthesising 3D brain MRA images given other multi-contrast 3D brain MR images as inputs. The developed system itself is however agnostic to the anatomical region captured in the images and may be used to synthesise MRA images of other organs and anatomical regions such as thoracic MRA images for example, given suitable training data.

By way of example, the images in the IXI data set were acquired using 1.5 Tesla and 3 Tesla Siemens MR scanners with the following acquisition parameters—T1-weighted images: transverse excitation (TE)=4.6 ms, transverse relaxation (TR)=9.6-9.8 ms, flip angle=8 degrees; T2-weighted images: TE=100 ms, TR=5725.8 ms-8178.3 ms, flip angle=90 degrees; PD-weighted images: TE=8 ms, TR=8178.3 ms, flip angle=90 degrees; and MRA images: TE=5.7-6.9 ms, TR=16.7-20 ms, flip angle=16 degrees-25 degrees. The T1-, T2-, and PD-weighted images have a spatial resolution of 0.94×0.94×1.2 mm$^3$ while the MRA images have a spatial resolution of 0.5×0.5×0.8 mm$^3$. A total of 486 subjects' images are available in the IXI database with required MR contrast images per subject, i.e. T1-weighted, T2-weighted, PD-weighted and MRA images. Data from these subjects were split randomly into 340 subjects' data for training, 50 subjects' data for validation and 96 subjects' data for testing.

By way of another example, the images from the MIDAS data set comprised multi-contrast MR images that were all acquired on a 3 Tesla Siemens Allegra MR scanner. Images were acquired Images from the MIDAS data set comprised T1-, T2-weighted images and MRA images from 78 subjects, which were all acquired on a 3 Tesla Siemens Allegra MR scanner. Images were acquired using the following acquisition parameters-T1-weighted images: TE=4.38 ms, TR=1700 ms, flip angle=8 degrees; T2-weighted images: TE=80 ms, TR=7730 ms, flip angle=180 degrees; and MRA images: TE=3.56 ms, TR=35 ms, flip angle=22 degrees. The T1- and T2-weighted images were acquired at a spatial resolution of 1×1×1 mm³, while the MRA images were acquired at a spatial resolution of 0.5×0.5×0.8 mm³. The disclosed system was pre-trained on the IXI data and then fine-tuned on data from 53 subjects available in the MIDAS database, to adapt its learned features and improve its performance at synthesising MRA images, given T1-weighted and T2-weighted MR images from the MIDAS database as inputs. 25 subjects' data from MIDAS were used for testing the fine-tuned system described in the present disclosure.

By way of a further example, the SIMON data set comprised images acquired from a single individual, across 12 different imaging/clinical sites, using a variety of MR scanners manufactured by different vendors, namely, Philips, Siemens and GE. Multiple observations from the same individual were acquired at different times, across different sites. The acquisition protocol at each site included: acquisition of T1-weighted MR image at a spatial resolution of 1×1×1 mm³ and either a PD-weighted or T2-weighted MR scan at a spatial resolution of 0.9×0.9×3.0 mm³. Full details of all acquisition parameters used in each imaging site are available on the CDIP website (https://www.cdip-pcid.ca/). No MRA images were acquired for this individual at any of the imaging sites. Consequently, the imaging data available from the SIMON database were used purely for evaluating the trained system, by synthesising MRA images using the other multi-contrast MR images available from each imaging site.

The disclosed system may be implemented using PyTorch or Tensorflow libraries on a PC with an suitable processing device, for example, a graphics processing unit (GPU) such as an NVIDIA RTX graphics processing unit. In a particular example, the disclosed system was trained using an Adam optimizer with an initial learning rate of $1\times10^{-4}$, which was used to minimise the complete loss function $\mathcal{L}_{complete}$ presented in equation (13). The decay rates of the gradient estimates' first and second momentum were hyperparameters of the Adam optimiser that were tuned empirically and in one example were set to 0 and 0.9, respectively. The weighting factors controlling the influence of different loss terms in $\mathcal{L}_{complete}$ were also hyperparameters that were tuned empirically and in one example were initialised to: $\lambda_1=300$, $\lambda_2=10$, $\lambda_3=10$, $\lambda_4=10$ and $\lambda_5=10$. Following the first ten epochs or iterations of training, $\lambda_1$ was adjusted to 30, while the rest remained unchanged. Tuning of all hyperparameters was undertaken using data from the validation set, partitioned from the data available in IXI, following a grid-search strategy to determine the most suitable combination of values for all hyperparameters. The parameters of all constituent network branches in the disclosed system may be learned iteratively, for example via the error back-propagation algorithm. Once trained, a forward-pass of inputted multi-contrast MR images, i.e. where the learned parameters of the networks in the disclosed system are fixed and only used for prediction, results in a synthesised MRA image, specific to the individual whose multi-contrast MR images were inputted to the system.

The disclosed system was trained and evaluated using data from different sources in individual experiments. Imaging data from the IXI database formed the main source for training the disclosed system and for preliminary testing of its performance in terms of the quality of MRA images synthesised. Subsequently, once the system was pre-trained on data from IXI, it was fine-tuned using data from MIDAS and was also evaluated in terms of its performance at synthesising MRA images given only T1-weighted and T2-weighted MR images as inputs. Finally, the pre-trained system (pre-trained on data from IXI) was also evaluated on data from the SIMON database. As no MRA images are available in the SIMON database, the disclosed system was not fine-tuned using this data but rather just used to 'infer' or predict MRA images given other multi-contrast MR images as inputs. Specifically, the multi-contrast MR images from each centre comprised either a pair of T1- and T2-weighted images or T1- and PD-weighted, which were inputted to the system and used to synthesise MRA images for the same individual.

The conducted experiments were used to demonstrate that the disclosed system may be trained with any combination of multi-contrast structural MR images as inputs (i.e. T1-weighted, T2-weighted, and/or PD-weighted) to synthesise MRA images for the corresponding subjects/individuals. The conducted experiments also served to demonstrate that the disclosed system is robust to variations in types/models of MR scanners and variations in image acquisition protocols. Specifically, this shows that the disclosed system, once trained might be directly applied or fine-tuned, given new data from a separate new imaging database, to synthesise MRA images that are adapted to the individuals/subjects' whose data are contained with the new imaging database. For instance, the trained system may be used to synthesise MRA images from large-scale population imaging databases such as the UK Biobank, which contain >50k subjects' structural brain MR contrast images (e.g. T1-weighted and T2-weighted) but lack MRA images for the corresponding individuals. Using the trained system disclosed herein to synthesise MRA images for such large population imaging databases may allow large-scale cohorts of MRA images and/or geometries of brain blood vessels extracted from the synthesised MRA images, to be curated. The disclosed system may also be trained for paired single-image-to-single-image synthesis wherein MRA images are synthesised from just one inputted MR contrast image (e.g. T1-weighted or T2-weighted or PD-weighted), for example. Additionally, the disclosed system is agnostic to both the anatomical region/organ captured within the field of view of the source and target domain images and is agnostic to the modality of the images. In other words, the disclosed system may be trained and used for synthesising other target imaging modalities that capture details of blood vessels such as contrast-enhanced computed tomography angiography (CTA), given suitable training data. Synthesis of images from other modalities using the disclosed system, such as CTA, may be achieved using a variety of source domain imaging modalities during training and subsequently inference/prediction. For example, the disclosed system may be trained to synthesise brain CTA images that highlight blood vessels, given non-contrast-enhanced head computed tomography (CT) images as input source domain images. Alternatively, the disclosed system may also be trained to synthesise brain CTA images from structural multi-contrast MR images (such as T1-weighted, T2-weighted and/or PD-weighted images), given suitable training data.

Similarly, as the disclosed system is agnostic to the anatomical region/organ captured within the field of view of the source and target domain images, it may also be trained and used to synthesise MRA images of the thoracic and/or abdominal regions, given structural multi-contrast MR images of the corresponding anatomical regions as inputs. For example, thoracic MRA images that capture fine details of the great vessels of the heart (e.g. aorta, pulmonary artery) may be synthesised by training the disclosed system to learn a mapping between suitable source domain images (e.g.

thoracic T1-weighted and/or T2-weighted MR images, or thoracic CT images) and the target domain MRA images, in a subject-specific manner. The disclosed system may also be used to synthesise other imaging modalities that highlight blood vessels such as fluorodeoxyglucose (FDG)-positron emission tomography from imaging modalities that capture non-vascular anatomical structures, tissues and organs (e.g. CT, multi-contrast MR images).

The disclosed system may be used to impute or 'fill in' or synthesise missing MRA images in large population studies, wherein, some proportion of subjects in the population are missing MRA images due to issues during image acquisition and/or data corruption or mishandling of data, among other reasons. MRA images synthesised using the disclosed system may be used to extract geometries of brain blood vessels, by representing vascular boundaries as triangular surface meshes or unstructured graphs. Brain vascular geometries were extracted from synthesised MRA images as an example of the present disclosure and the morphological and haemodynamic characteristics of the synthetic vascular geometries were compared against vascular geometries extracted from their corresponding real MRA image counterparts. Comparing morphological properties between the synthetic and real vascular geometries across all subjects in the test sets showed no statistically significant differences were present between the synthetic and real geometries. Haemodynamic characteristics of the synthetic and real vascular geometries were also evaluated and compared by running computational fluid dynamics simulations of blood flow using the extracted synthetic and real vascular geometries. Key haemodynamic variables such as local velocity directions, magnitude, and wall shear stresses were compared and found to show no significant differences between the synthetic and real vascular geometries for each subject included in the evaluation. Preservation of key morphological and haemodynamic characteristics demonstrates that the disclosed system may be used to synthesise brain MRA images from other multi-contrast structural MR images in a manner that enables vascular geometries derived thereof, to be used in in-silico trials and/or observation studies.

The disclosed system may also provide a method for designing, or testing neurovascular medical devices (e.g. flow diverters, stents, intra-saccular coils, etc.), comprising: training the brain MRA image synthesis system using patients' multi-contrast brain MR images as inputs (e.g. T1-weighted, T2-weighted and/or PD-weighted images), synthesising MRA images for new patients lacking real MRA images when given their structural multi-contrast MR images as inputs, extracting brain vascular geometries from the synthesised MRA images, curating a population of synthetic brain vascular geometries from synthesised MRA images, designing the medical device using the synthetic population of vascular geometries or testing the medical device using the synthetic population of vascular geometries. Accordingly, examples of the present application provide a way of generating synthetic populations of brain vasculature (for, e.g., IST-based testing of medical devices against), that preserve key anatomical and physiological characteristics relative to brain vascular geometries derived from real MRA images when available. Examples of the present application also provide a way of generating synthetic populations of brain vasculature representative of a myriad of different potential target patient populations, to enable meaningful assessment of the respective medical device performance.

Examples according to the present disclosure may be used in any in-silico studies, including, but not limited to in-silico trials and observation studies, as used to develop medical devices such as implants meant for use in or on the patient body, but also drug development and general medical devices (including, for example, digital heath products, AI-based medical software and the like). Put another way, examples may be used with any sort of in-silico study.

The disclosed system may also provide a method for designing or testing software systems designed for neurological image-guided interventions, such as neurosurgical operations or implantation of neurological devices including neurodiagnostics, neurointerventional and neurostimulation devices. Accordingly, examples of the present application provide a way of enriching existing databases of MRA images of patients, by synthesising MRA images of patients that lack MRA image acquisitions but do have other structural multi-contrast MR images. Enriched databases of MRA images (by augmenting with synthesised MRA images) would allow software systems designed for neurological image-guided interventions to be designed and tested retrospectively on wider populations than afforded by relying on real MRA images alone. This is particularly significant given the high prevalence of T1-weighted and T2-weighted images that are acquired as part of routine imaging protocols in hospitals across the world, but the relative scarcity of MRA images acquired at the same sites.

Figure 11:
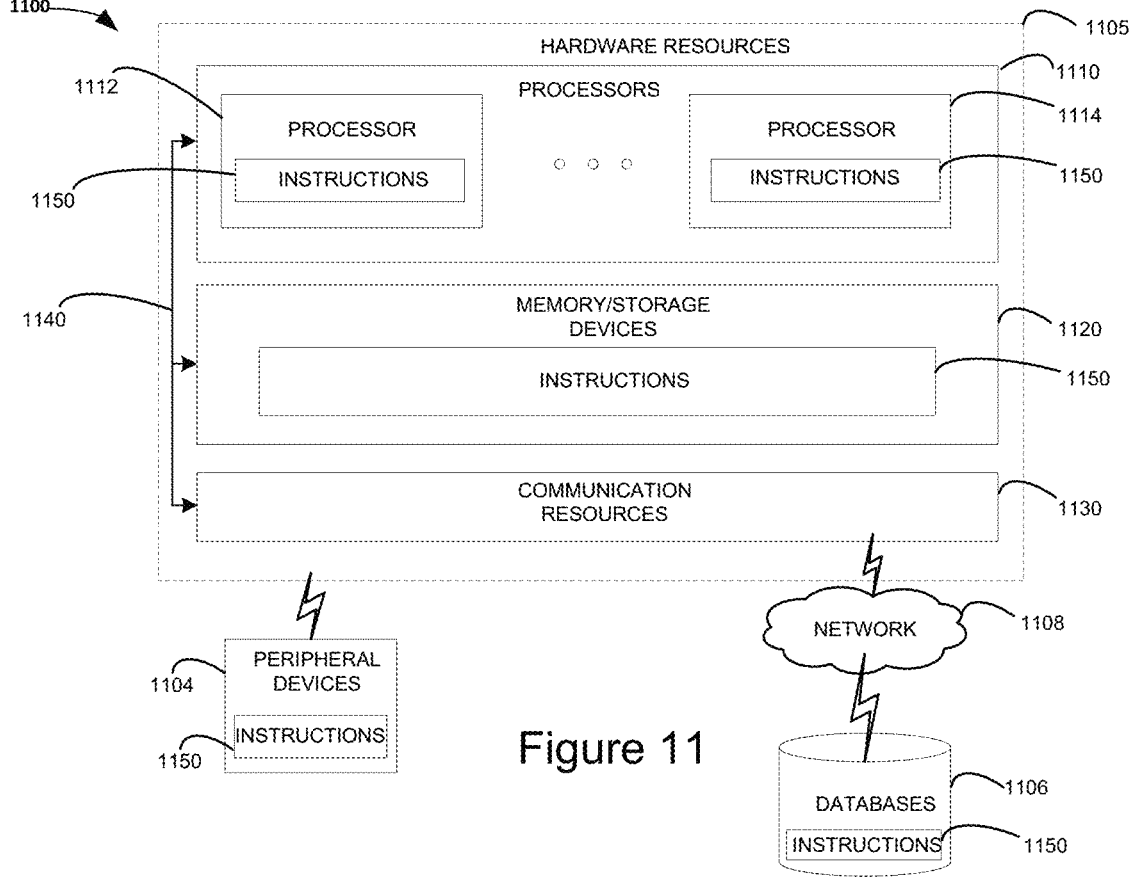
FIG. 11 shows an example hardware implementation the system of FIG. 1, according to an example of the disclosure.

Examples of the present disclosure may be implemented by suitably programmed computer hardware. FIG. 11 is a block diagram 1100 illustrating components, according to some example embodiments, able to read instructions from a machine-readable or computer-readable medium (e.g., a non-transitory machine-readable storage medium) and perform any one or more of the methodologies discussed herein, hence providing the apparatus or system to carry out the described MRA image generation. Specifically, FIG. 11 shows a diagrammatic representation of hardware resources 1105 including one or more processors (or processor cores) 1110, one or more memory/storage devices 1120, and one or more communication resources 1130, each of which may be communicatively coupled via a bus 1140. The processors 1110 (e.g., a central processing unit (CPU), a reduced instruction set computing (RISC) processor, a complex instruction set computing (CISC) processor, a graphics processing unit (GPU), a digital signal processor (DSP) such as a baseband processor, an application specific integrated circuit (ASIC), a cloud processing function (such as AWS instance), another processor, or any suitable combination thereof) may include, for example, a processor 1112 and a processor 1114.

The memory/storage devices 1120 may include main memory, disk storage, or any suitable combination thereof. The memory/storage devices 1120 may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, solid-state storage device (SSD), magnetic storage based hard disk drive (HDD) media, etc.

The communication resources 1130 may include interconnection or network interface components or other suitable devices to communicate with one or more peripheral devices 1104 or one or more databases 1106 via a network 1108. For example, the communication resources 1130 may include wired communication components (e.g., for coupling via Ethernet, a Universal Serial Bus (USB) or the like), cellular communication components, NFC components, Bluetooth® components (e.g., Bluetooth® Low Energy), Wi-Fi® components, and other communication components.

Instructions 1150 may comprise software, a program, an application, an applet, an app, or other executable code for causing at least any of the processors 1110 to perform any one or more of the methodologies discussed herein. The instructions 1150 may reside, completely or partially, within at least one of the processors 1110 (e.g., within the processor's cache memory), the memory/storage devices 1120, or any suitable combination thereof. Furthermore, any portion of the instructions 1150 may be transferred to the hardware resources 1105 from any combination of the peripheral devices 1104 or the databases 1106. Accordingly, the memory of processors 1110, the memory/storage devices 1120, the peripheral devices 1104, and the databases 1106 are examples of computer-readable and machine-readable media.

In some embodiments, the electronic device(s), network(s), system(s), chip(s) or component(s), or portions or implementations thereof, of FIGS. 11, or some other figure herein may be configured to perform one or more processes, techniques, or methods as described herein, or portions thereof.

In the foregoing, functions are described as modules or blocks, i.e. functional units that are operable to carry out the described function, algorithm, or the like. These terms may be interchangeable. Where modules, blocks, or functional units have been described, they may be formed as processing circuitry, where the circuitry may be general purpose processor circuitry configured by program code to perform specified processing functions. The circuitry may also be configured by modification to the processing hardware. Configuration of the circuitry to perform a specified functions may be entirely in hardware, entirely in software or using a combination of hardware modification and software execution. Program instructions may be used to configure logic gates of general purpose or special-purpose processor circuitry to perform a processing function.

Circuitry may be implemented, for example, as a hardware circuit comprising custom Very Large Scale Integrated, VLSI, circuits or gate arrays, off-the-shelf semiconductors such as logic chips, transistors, or other discrete components. Circuitry may also be implemented in programmable hardware devices such as field programmable gate arrays, FPGA, programmable array logic, programmable logic devices, A System on Chip, SoC, or the like.

Machine readable program instructions may be provided on a transitory medium such as a transmission medium or on a non-transitory medium such as a storage medium. Such machine readable instructions (computer program code) may be implemented in a high level procedural or object oriented programming language. However, the program(s) may be implemented in assembly or machine language, if desired. In any case, the language may be a compiled or interpreted language, and combined with hardware implementations. Program instructions may be executed on a single processor or on two or more processors in a distributed manner.

Examples provide a computer-implemented method for synthesising (i.e. generating) magnetic resonance angiography (MRA) images from other types of inputted magnetic resonance (MR) images, in a subject-specific manner, the method comprising providing a conditional generative adversarial network (cGAN) that learns a combined latent representation of the inputted magnetic resonance images for each subject and learns to transform this combined latent representation to a magnetic resonance angiography image corresponding to that subject, providing a plurality of magnetic resonance (MR) images as input into the cGAN, and outputting a plurality of MRA images from the cGAN based on the plurality of inputted MR images.

In some examples, the cGAN comprises a Generator network that learns a combined latent representation of the inputted MR images for each subject and learns to transform the latent representation to MRA images for each corresponding subject.

In some examples, the Generator network comprises a convolutional encoder-decoder network architecture operable to learn to transform any combination of inputted MR images of a given subject to an MRA image specific to that subject.

In some examples, the cGAN further comprises a Discriminator network operating at a single or multiple spatial scales/resolution, to compete with the Generator network and improve the performance of the Generator network at synthesising MRA images using a loss function.

In some examples, the Discriminator network is used in combination with any pre-trained convolutional neural network to determine perceptual losses that are used to train the cGAN.

In some examples, the data inputted to the Discriminator network to compute feature matching losses, that are used to train the cGAN, are any combination of real and/or synthesised MRA images in their native 3D domain, or their 2D projection domains.

In some examples, the Discriminator network comprises a Multi-scale Discriminator network comprising two sub-networks, wherein a first sub-network operates at a higher scale/resolution and wherein a second sub-network operates at a lower spatial scale/resolution, wherein the two sub-networks are trained using a modified version of the least-squares adversarial loss function.

In some examples, an overall loss function, $\mathcal{L}_{overall}$, comprises:

$$\mathcal{L}_{overall} = \mathcal{L}_{cGAN}(G, D) + \mathcal{L}_{recon}; \tag{2}$$

wherein the Loss function, $\mathcal{L}_{cGAN}(G, D_k)$, of the Discriminator network comprises:

$$L_{cGAN}(G, D_k) = -\mathbb{E}_{I_N, y}\left[(D_k(I_n, y) - 1)^2\right] - \mathbb{E}_{I_N}\left[D_k(I_n, G(I_n))^2\right] \tag{6}$$

and
wherein the reconstruction Loss, $\mathcal{L}_{recon}$, comprises:

$$\mathcal{L}_{recon} = \mathbb{E}_{I_N, y}[\|y - G(I_n)\|_1] \text{ or } \mathcal{L}_{recon} = \mathbb{E}_{I_N, y}[\|y - G(I_n)\|_2] \tag{3}$$

In some examples, the Discriminator network $D_k$ comprises a multi-scale Discriminator network and wherein the method further comprises use of a feature matching loss $\mathcal{L}_{FM3D}$ that minimises a difference in feature representations at intermediate layers of the multi-scale Discriminator network $D_k$ and is formulated as:

$$\mathcal{L}_{FM3D}(G, D_k) = \mathbb{E}_{I_N, y}\sum_{i=1}^{L} \frac{1}{N_i}\left[\|D_k^i(I_n, y) - D_k^i(I_n, G(I_n))\|_1\right] \tag{7}$$

In some examples, the loss function comprises a plurality of 2D projection MRA domain-specific perceptual loss terms that act on maximum intensity projection images along three different axes: axial, coronal and sagittal.

In some examples, the respective 2D projection perceptual loss terms are given by the equations:

$$\mathcal{L}_{PER2D-axial}(G, V) = \tag{9}$$
$$\mathbb{E}_{I_N, y} \sum\nolimits_{f=1}^{F} \frac{1}{M_f} \left[ \left\| V^f(p_{axial}(y)) - V^f(p_{axial}(G(I_n))) \right\|_1 \right],$$

$$\mathcal{L}_{PER2D-coronal}(G, V) = \tag{10}$$
$$\mathbb{E}_{I_N, y} \sum\nolimits_{f=1}^{F} \frac{1}{M_f} \left[ \left\| V^f(p_{coronal}(y)) - V^f(p_{coronal}(G(I_n))) \right\|_1 \right],$$

$$\mathcal{L}_{PER2D-sagittal}(G, V) = \tag{11}$$
$$\mathbb{E}_{I_N, y} \sum\nolimits_{f=1}^{F} \frac{1}{M_f} \left[ \left\| V^f(p_{sagittal}(y)) - V^f(p_{sagittal}(G(I_n))) \right\|_1 \right],$$

In some examples, the loss function further comprises a 3D volume component, said 3D loss function component comprising:

$$\mathcal{L}_{PER3D}(G, V) = \mathbb{E}_{I_N, y} \sum\nolimits_{f=1}^{F} \frac{1}{M_f} \left[ \left\| V^f(y) - V^f(G(I_n)) \right\|_1 \right], \tag{8}$$

In some examples, the loss function comprises feature matching loss terms and a perceptual loss terms, and wherein these are combined to formulate a combined reconstruction loss $\mathcal{L}_{recon}$ comprising the equation:

$$\mathcal{L}_{recon} = \tag{12}$$
$$\lambda_1 \left[ \sum\nolimits_{k=1}^{2} \mathcal{L}_{FM3D}(G, D_k) \right] + \lambda_2 \mathcal{L}_{PER3D}(G, V) + \lambda_3 \mathcal{L}_{PER2D-axial}(G, V) +$$
$$\lambda_4 \mathcal{L}_{PER2D-coronal}(G, V) + \lambda_5 \mathcal{L}_{PER2D-sagittal}(G, V)$$

where, $\lambda_1$, $\lambda_2$, $\lambda_3$, $\lambda_4$ and $\lambda_5$ represent weights that control the influence of each feature matching or perceptual loss term in $\mathcal{L}_{recon}$ on an overall learning process of the method.

In some examples, a complete loss function used to train the cGAN in an end-to-end fashion is given by the equation:

$$\mathcal{L}_{complete} = \min_G \left[ \left[ \max_{D1, D2} \sum\nolimits_{k=1}^{2} \mathcal{L}_{cGAN}(G, D_k) \right] + \mathcal{L}_{recon} \right] \tag{13}$$

Examples also provide a computer readable medium comprising instructions, which, when carried out by one or more processors, cause the one or more processors to carry out any of the described methods.

Examples also provide a method of developing medical devices or medicines comprising deriving generated MRA images for testing medical devices or medicines under development from real MRI images using any of the described methods and testing the medical devices or medicines using the generated MRA images.

In some examples, the anatomical coverage shown in the original T1/T1/PD-weighted images used may be a consequence of the modality of use. Thus the different imaging modalities are capable of detecting different parameters of the patient or organ under study, such that a complete patient can be modelled by combining data from more than one modality, into the resultant MRA images. For example, even if modalities are looking at the same field of view, they can detect different aspects of the parts of the patient within that same field of view. By way of a specific example, a first modality may be able to image (i.e. "see") the muscular structure, and another modality may be able to image the vascular structure. Put another way, by enabling the generation of MRA images by effectively 'mixing' of patient imaging modalities, a complete MRA image may be provided that did not otherwise exist in the original imaging dataset. As such, examples of the present disclosure allows use of previously acquired, but not complete, imaging data sets. The different imaging modalities may comprise any one or more of: magnetic resonance imaging (including cross-sectional, angiographic, or any variant of structural, functional or molecular imaging), computed tomography (including cross-sectional, angiographic, or any variant of structural, or functional imaging), ultrasound (including any variant of structural or functional), positron emission tomography, single-photon emission tomography. Each of these imaging techniques may be enhanced with appropriate endogenous or exogenous contrast media to highlight the anatomical or functional structures of interest.

Examples also provide a computer readable medium comprising instructions, which, when executed by one or more processors, causes the one or more processors to carry out any of the described methods, or parts thereof (e.g. method of deriving MRA images of subjects from other modality images for the same subject with the trained system).

Examples also provide an apparatus arranged or configured to carry out any of the described methods.

Examples according to the present disclosure may be used in any in-silico studies, including, but not limited to in-silico trials and observation studies, as used to develop medical devices such as implants meant for use in or on the patient body, but also drug development and general medical devices (including, for example, digital heath products, AI-based medical software and the like). Put another way, examples may be used with any sort of in-silico study.

Accordingly, examples of the present disclosure feed into the medical development process, because they can provide an improved method of designing or testing a device for use in, or drug for use on, a human organ, preferably the brain, that makes use of the synthesised MRA images.

Examples of the present disclosure may be used to derive a plurality of in-silico virtual test patients to test the device or drug on virtually. Such test patients may be used for testing a plurality of versions of a given medical device, or drug, virtually on the plurality of virtual patients to derive a plurality of test results, from which parameters about the tested medical device or drug may be derived. Those derived parameters of the tested medical device or drug may in turn be used to deriving a final form of device or drug from the plurality of test results. Those derived parameters of the tested medical device or drug may equally be the performance parameters of a final form of medical device or drug.

While preferred embodiments of the present invention have been shown and described herein, it will be obvious to those skilled in the art that such embodiments are provided by way of example only. Numerous variations, changes, and substitutions will now occur to those skilled in the art without departing from the scope of the disclosure. It should be understood that various alternatives to the embodiments of the invention described herein may be employed in any combination in practicing the disclosure. It is intended that the following claims define the scope of the invention and that methods and structures within the scope of these claims and their equivalents be covered thereby.

The invention claimed is:

1. A computer-implemented method for synthesising magnetic resonance angiography (MRA) images from other types of inputted magnetic resonance (MR) images, in a subject-specific manner, the method comprising:

providing a conditional generative adversarial network (cGAN) that learns a combined latent representation of the inputted magnetic resonance images for each subject and learns to transform this combined latent representation to a magnetic resonance angiography image corresponding to that subject;

providing a plurality of magnetic resonance (MR) images as input into the cGAN; and outputting a plurality of MRA images from the cGAN based on the plurality of inputted MR images;

wherein the cGAN comprises:

a Generator network that learns a combined latent representation of the inputted MR images for each subject and learns to transform the latent representation to MRA images for each corresponding subject, a Discriminator network operating at a single or multiple spatial scales/resolution, to compete with the Generator network and improve the performance of the Generator network at synthesising MRA images using a loss function, and wherein the loss function comprises a plurality of 2D projection MRA domain-specific perceptual loss terms that act on maximum intensity projection images along three different axes: axial, coronal and sagittal.

2. The method of claim 1, wherein the Generator network comprises a convolutional encoder-decoder network architecture operable to learn to transform any combination of inputted MR images of a given subject to an MRA image specific to that subject.

3. The method of claim 1, wherein the Discriminator network is used in combination with any pre-trained convolutional neural network to determine perceptual losses that are used to train the cGAN.

4. The method of claim 1, wherein data inputted to the Discriminator network to compute feature matching losses, that are used to train the cGAN, are any combination of real and/or synthesised MRA images in their native 3D domain, or their 2D projection domains.

5. The method of claim 1, wherein the Discriminator network comprises a Multi-scale Discriminator network comprising two sub-networks, wherein a first sub-network operates at a higher scale/resolution and wherein a second sub-network operates at a lower spatial scale/resolution, wherein the two sub-networks are trained using a modified version of the least-squares adversarial loss function.

6. The method of claim 5, wherein an overall loss function, $\mathcal{L}_{overall}$, comprises:

$$\mathcal{L}_{overall} = \mathcal{L}_{cGAN}(G,D) + \mathcal{L}_{recon} \qquad (2):$$

wherein the Loss function, $\mathcal{L}_{cGAN}(G, D_k)$, of the Discriminator network comprises:

$$\mathcal{L}_{cGAN}(G, D_k) = -\mathbb{E}_{I_N,y}\left[(D_k(I_n, y) - 1)^2\right] - \mathbb{E}_{I_N}\left[D_k(I_n, G(I_n))^2\right] \qquad (6)$$

and wherein the reconstruction Loss, $\mathcal{L}_{recon}$, comprises:

$$\mathcal{L}_{recon} = \mathbb{E}_{I_N,y}[\|y - G(I_n)\|_1] \text{ or } \mathcal{L}_{recon} = \mathbb{E}_{I_N,y}[\|y - G(I_n)\|_2]. \qquad (3)$$

7. The method of claim 1, wherein the Discriminator network $D_k$ comprises a multi-scale Discriminator network and wherein the method further comprises use of a feature matching loss $\mathcal{L}_{FM3D}$ that minimises a difference in feature representations at intermediate layers of the multi-scale Discriminator network DR and is formulated as:

$$\mathcal{L}_{FM3D}(G, D_k) = \mathbb{E}_{I_N,y}\sum_{l=1}^{L}\frac{1}{N_l}\left[\left\|D_k^i(I_n, y) - D_k^i(I_n, G(I_n))\right\|_1\right]. \qquad (7)$$

8. The method of claim 1, wherein the respective 2D projection perceptual loss terms are given by the equations:

$$\mathcal{L}_{PER2D-axial}(G, V) = \qquad (9)$$
$$\mathbb{E}_{I_N,y}\sum_{f=1}^{F}\frac{1}{M_f}\left[\left\|V^f(p_{axial}(y)) - V^f(p_{axial}(G(I_n)))\right\|_1\right],$$

$$\mathcal{L}_{PER2D-coronal}(G, V) = \qquad (10)$$
$$\mathbb{E}_{I_N,y}\sum_{f=1}^{F}\frac{1}{M_f}\left[\left\|V^f(p_{coronal}(y)) - V^f(p_{coronal}(G(I_n)))\right\|_1\right],$$

$$\mathcal{L}_{PER2D-sagittal}(G, V) = \qquad (11)$$
$$\mathbb{E}_{I_N,y}\sum_{f=1}^{F}\frac{1}{M_f}\left[\left\|V^f(p_{sagittal}(y)) - V^f(p_{sagittal}(G(I_n)))\right\|_1\right].$$

9. The method of claim 1, wherein the loss function further comprises a 3D volume component, said 3D loss function component comprising:

$$\mathcal{L}_{PER3D}(G, V) = \mathbb{E}_{I_N,y}\sum_{f=1}^{F}\frac{1}{M_f}\left[\left\|V^f(y) - V^f(G(I_n))\right\|_1\right]. \qquad (8)$$

10. The method of claim 1, wherein the loss function comprises feature matching loss terms and a perceptual loss terms, and wherein these are combined to formulate a combined reconstruction loss $\mathcal{L}_{recon}$ comprising the equation:

$$\mathcal{L}_{recon} = \qquad (12)$$
$$\lambda_1\left[\sum_{k=1}^{2}\mathcal{L}_{FM3D}(G, D_k)\right] + \lambda_2\mathcal{L}_{PER3D}(G, V) + \lambda_3\mathcal{L}_{PER2D-axial}(G, V) +$$
$$\lambda_4\mathcal{L}_{PER2D-coronal}(G, V) + \lambda_5\mathcal{L}_{PER2D-sagittal}(G, V)$$

where, $\lambda_1$, $\lambda_2$, $\lambda_3$, $\lambda_4$ and $\lambda_5$ represent weights that control the influence of each feature matching or perceptual loss term in $\mathcal{L}_{recon}$ on an overall learning process of the method.

11. The method of claim 1, wherein a complete loss function used to train the cGAN in an end-to-end fashion is given by the equation:

$$\mathcal{L}_{complete} = \min_{G}\left[\left[\max_{D1,D2}\sum_{k=1}^{2}\mathcal{L}_{cGAN}(G, D_k)\right] + \mathcal{L}_{recon}\right]. \qquad (13)$$

12. A non-transitory computer readable medium comprising instructions, which, when carried out by one or more processors, cause the one or more processors to carry out the method of claim 1.

13. A method of developing medical devices or medicines comprising:

deriving generated MRA images for testing medical devices or medicines under development from real MRI images using the method of claim 1; and testing the medical devices or medicines using the generated MRA images.

* * * * *